United States Patent
Takeshima

(10) Patent No.: US 11,615,880 B2
(45) Date of Patent: Mar. 28, 2023

(54) MEDICAL DATA PROCESSING APPARATUS, MEDICAL DATA PROCESSING METHOD, AND MEDICAL IMAGE DIAGNOSTIC APPARATUS

(71) Applicant: Canon Medical Systems Corporation, Otawara (JP)

(72) Inventor: Hidenori Takeshima, Kawasaki (JP)

(73) Assignee: Canon Medical Systems Corporation, Otawara (JP)

( * ) Notice: Subject to any disclaimer, the term of this patent is extended or adjusted under 35 U.S.C. 154(b) by 301 days.

(21) Appl. No.: 16/996,969

(22) Filed: Aug. 19, 2020

(65) Prior Publication Data
US 2021/0057084 A1 Feb. 25, 2021

(30) Foreign Application Priority Data
Aug. 22, 2019 (JP) .............................. JP2019-152273

(51) Int. Cl.
*G16H 30/00* (2018.01)
*G16H 30/40* (2018.01)
(Continued)

(52) U.S. Cl.
CPC ........... *G16H 30/40* (2018.01); *A61B 5/0033* (2013.01); *A61B 5/055* (2013.01); *A61B 5/7232* (2013.01);
(Continued)

(58) Field of Classification Search
CPC ...... G16H 30/40; G06N 3/084; A61B 5/0033; A61B 5/055; A61B 5/7232; A61B 5/7257; A61B 5/7275; A61B 5/742
See application file for complete search history.

(56) References Cited

U.S. PATENT DOCUMENTS

| 8,953,862 B2 * | 2/2015 | Date ........................ G06K 9/00 382/131 |
| 10,712,416 B1 * | 7/2020 | Sandino ................ G06T 11/008 |

(Continued)

FOREIGN PATENT DOCUMENTS

| CA | 3030876 A1 * | 1/2018 | ......... G02B 17/0864 |
| JP | 2014-079443 A | 5/2014 | |
| JP | 2018-161349 A | 10/2018 | |

OTHER PUBLICATIONS

Kamamoto et al., "Lossless Compression of Multi-channel Signals Using Inter-channel Correlation", Information Processing Society Information Magazine, vol. 46, No. 5, May 2005, 11 pages (with English Abstract).

*Primary Examiner* — Khai M Nguyen
(74) *Attorney, Agent, or Firm* — Oblon, McClelland, Maier & Neustadt, L.L.P.

(57) ABSTRACT

A medical data processing apparatus according to one embodiment includes processing circuitry. The processing circuitry obtains a compressed channel of data generated by compressing a plurality of first medical channels of data defined by first domain representation and respectively corresponding to a plurality of components, via an intermediate channel of data defined by second domain representation. The processing circuitry decodes the compressed channel of data to a second medical channel of data defined by the first domain representation based on a conversion process from the plurality of first medical channels of data to the compressed dataset.

14 Claims, 12 Drawing Sheets

(51) Int. Cl.
*G06N 3/084* (2023.01)
*A61B 5/00* (2006.01)
*A61B 5/055* (2006.01)

(52) U.S. Cl.
CPC .......... *A61B 5/7257* (2013.01); *A61B 5/7275* (2013.01); *A61B 5/742* (2013.01); *G06N 3/084* (2013.01)

(56) References Cited

U.S. PATENT DOCUMENTS

| | | | |
|---|---|---|---|
| 2007/0014480 A1* | 1/2007 | Sirohey | H04N 19/62 382/128 |
| 2013/0011061 A1* | 1/2013 | Pan | H04N 19/423 382/173 |
| 2014/0211909 A1 | 7/2014 | Yamazaki et al. | |
| 2015/0071518 A1* | 3/2015 | Campagna | G16H 30/40 382/131 |
| 2018/0211356 A1 | 7/2018 | Kurahashi | |
| 2018/0277068 A1 | 9/2018 | Diederich et al. | |

\* cited by examiner

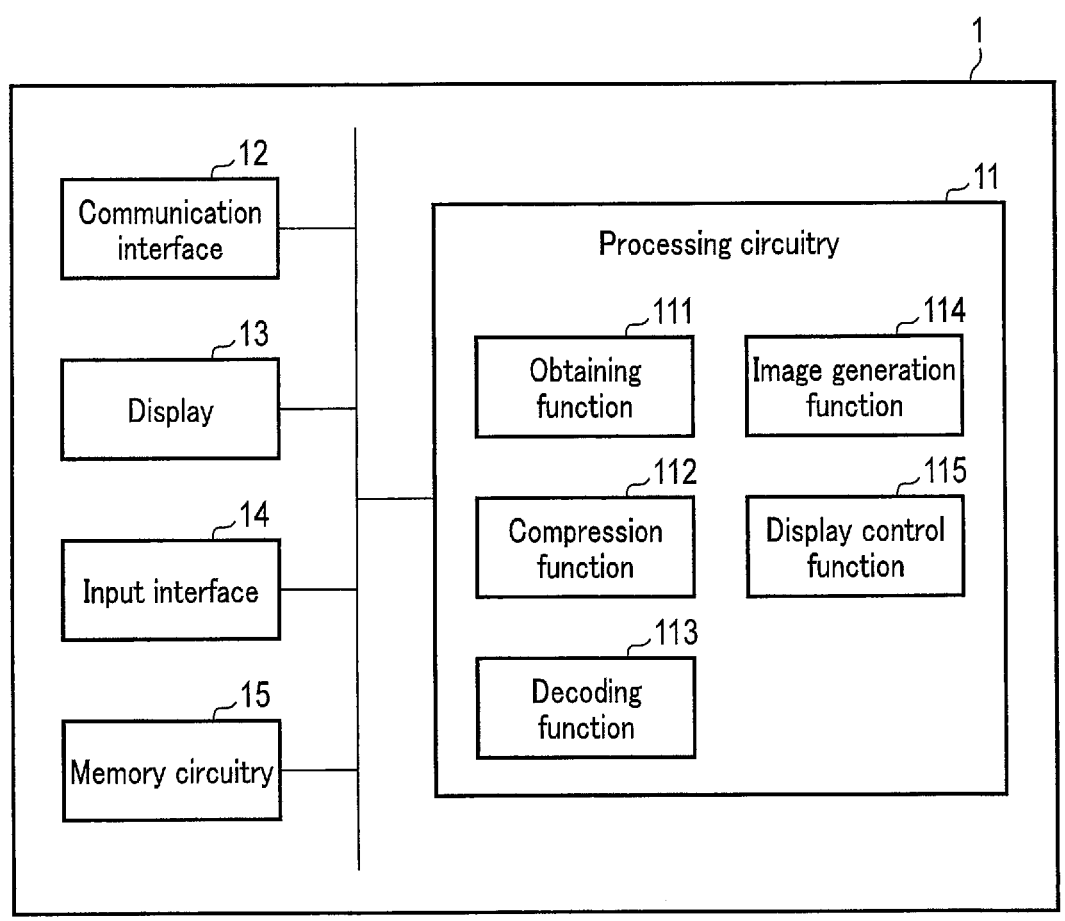
F I G. 1

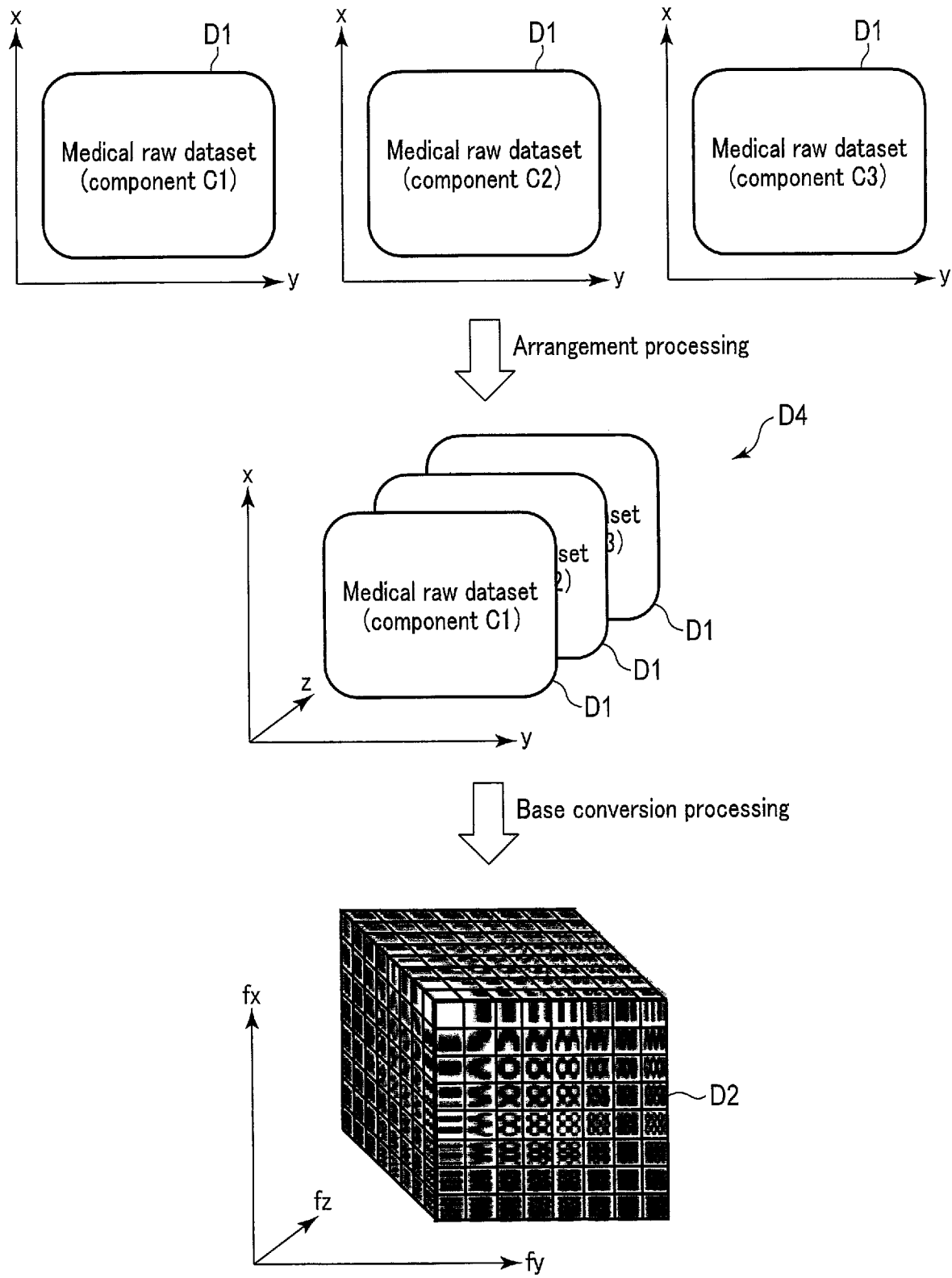
F I G. 3

Quantized dataset

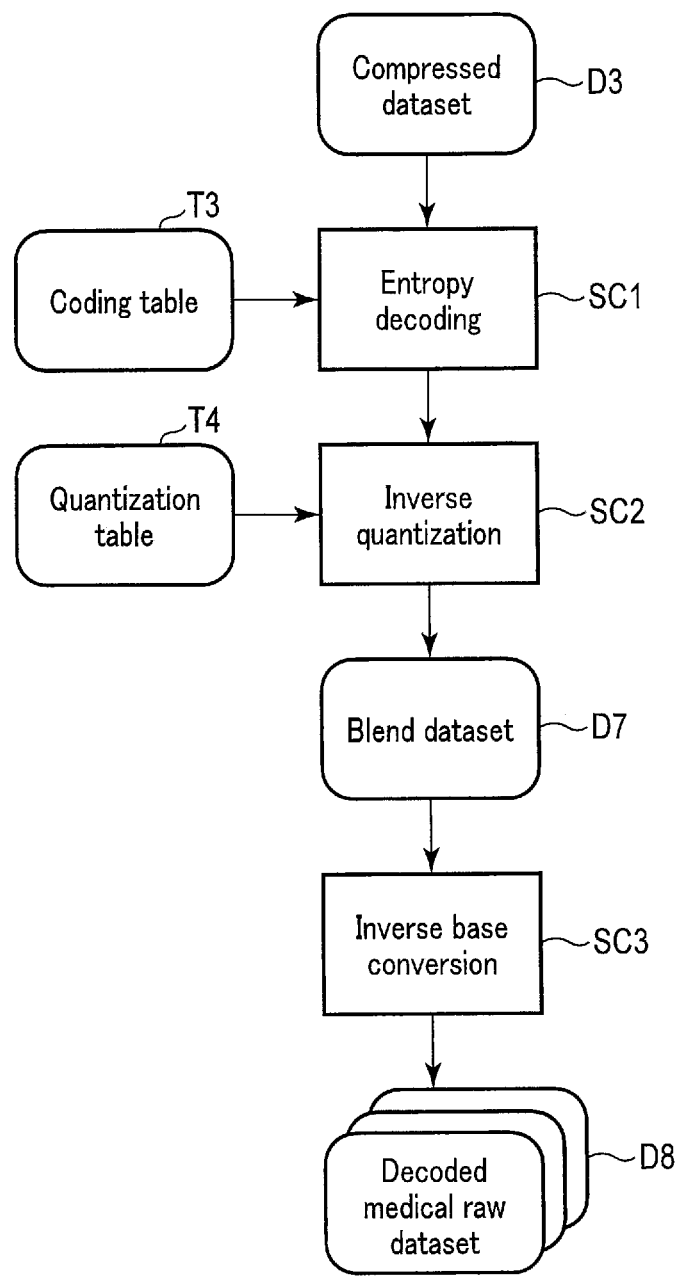
F I G. 10

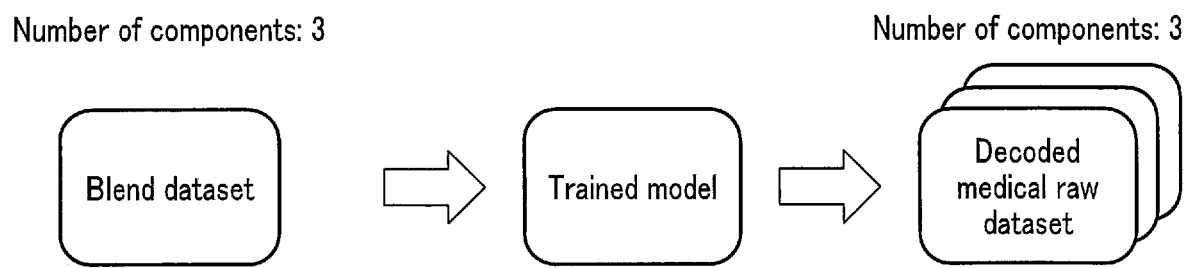
F I G. 11

MEDICAL DATA PROCESSING APPARATUS, MEDICAL DATA PROCESSING METHOD, AND MEDICAL IMAGE DIAGNOSTIC APPARATUS

CROSS-REFERENCE TO RELATED APPLICATIONS

This application is based upon and claims the benefit of priority from the Japanese Patent Application No. 2019-152273, filed Aug. 22, 2019, the entire contents of which are incorporated herein by reference.

FIELD

Embodiments described herein relate generally to a medical data processing apparatus, a medical data processing method, and a medical image diagnostic apparatus.

BACKGROUND

Accompanying an increase in an amount of medical data, compression and decoding are being performed on medical data. Multicomponent medical raw data is obtained through data acquisition with the use of dual-energy scanning in X-ray computed tomography (CT) or a plurality of receiver channels in magnetic resonance imaging (MRI). Since there is a large amount of such multicomponent medical raw data, more efficient compression and decoding are desired.

BRIEF DESCRIPTION OF THE DRAWINGS

FIG. 1 is a diagram showing a configuration of a medical data processing apparatus according to a present embodiment.

FIG. 3 is a schematic diagram showing base conversion, which is illustrated in FIG. 2.

FIG. 10 is a diagram showing a typical flow of decoding processing that the processing circuitry illustrated in FIG. 1 performs on a compressed dataset.

FIG. 11 is a schematic diagram showing a relationship between input and output of a trained model for decoding.

DETAILED DESCRIPTION

Figure 2:
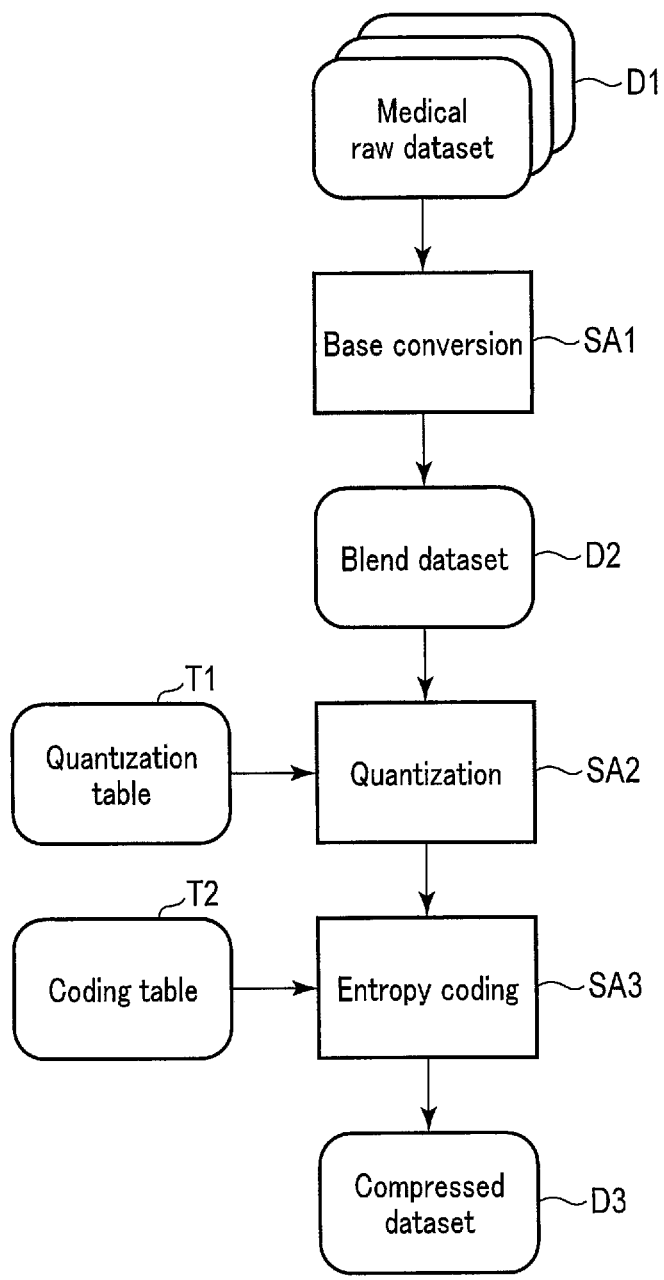
FIG. 2 is a diagram showing a typical flow of compression processing that processing circuitry illustrated in FIG. 1 performs on a medical raw dataset.

In general, according to one embodiment, a medical data processing apparatus includes processing circuitry. The processing circuitry obtains a compressed dataset generated by compressing a plurality of medical first datasets defined by first domain representation and respectively corresponding to a plurality of components, via an intermediate dataset defined by second domain representation. The processing circuitry decodes the compressed dataset to a second medical dataset defined by the first domain representation based on a conversion process from the plurality of first medical datasets to the compressed dataset.

Hereinafter, a medical data processing apparatus, medical data processing method, and a medical image diagnostic apparatus according to the present embodiment will be described with reference to the accompanying drawings.

The medical data processing apparatus according to the present embodiment corresponds to a computer configured to process medical data. Medical data corresponds to raw data (hereinafter referred to as medical raw data) or image data (hereinafter referred to as medical image data) collected by the medical image diagnostic apparatus. The medical image diagnostic apparatus may be a single-modality apparatus or a composite-modality apparatus. Examples of the single-modality apparatus include an X-ray computed tomography apparatus (CT apparatus), a magnetic resonance imaging apparatus (MRI apparatus), an X-ray diagnostic apparatus, a positron emission tomography (PET) apparatus, a single photon emission CT (SPECT) apparatus, and an ultrasonic diagnostic apparatus. Examples of the composite-modality apparatus include a PET/CT apparatus, a SPECT/CT apparatus, a PET/MRI apparatus, and a SPECT/MRI apparatus. Alternatively, the medical image diagnostic apparatus may be an optical interference tomographic apparatus or an ultrasonic diagnostic apparatus.

When the medical image diagnostic apparatus is a CT apparatus, a gantry of the CT apparatus applies X-rays to a subject from an X-ray tube while rotating the X-ray tube and an X-ray detector around the subject, and detects by the X-ray detector the X-rays passed through the subject. In the X-ray detector, an electric signal having a crest value corresponding to the detected X-ray dose is generated. This electric signal is subjected to signal processing such as A/D conversion by data acquisition circuitry. The A/D converted electrical signal is referred to as projection data or sinogram data. The projection data or sinogram data corresponds to a type of medical raw data.

When the medical image diagnostic apparatus is an MRI apparatus, a gantry of the MRI apparatus repeats application of the gradient magnetic field by way of a gradient magnetic field coil and application of RF pulses by way of a transmission coil under the application of the static magnetic field by way of a static magnetic field magnet. An MR signal from the subject is released in response to the application of the RF pulse. The released MR signal is received by way of a reception coil. The received MR signal is subjected to signal processing such as A/D conversion by the reception circuitry. The A/D converted MR signal is referred to as k-space data. The k-space data corresponds to a type of medical raw data.

When the medical image diagnostic apparatus is an ultrasonic probe of the ultrasonic diagnostic apparatus, the ultrasonic probe transmits ultrasonic beams from a plurality of ultrasonic vibrators into the subject body, and receives the ultrasonic waves reflected from the subject body by way of the ultrasonic vibrators. The ultrasonic vibrators generate an electric signal having a crest value corresponding to the sound pressure of the received ultrasonic waves. The electric signal is subjected to the A/D conversion by the A/D converter provided in the ultrasonic probe or the like. The A/D converted electric signal is referred to as echo data. The echo data is a type of medical raw data.

When the medical image diagnostic apparatus is a PET apparatus, a gantry of the PET apparatus simultaneously measures by simultaneous measurement circuitry a pair of gamma rays with 511 keV, which are generated in accordance with the annihilation of positrons generated from radionuclides accumulated in the subject and electrons around the radionuclide, thereby generating digital data having digital values indicative of the energy value and detection position of the pair of gamma rays. This digital data is referred to as coincidence data or sinogram data. The coincidence data or sinogram data is a type of medical raw data.

When the medical image diagnostic apparatus is an X-ray diagnostic apparatus, the irradiation is from the X-ray tube provided in the C-arm. The X-rays produced by the X-ray tube and transmitted through the subject are received by an X-ray detector such as a flat panel display (FPD) arranged in the C-arm or arranged separately from the C-arm. The X-ray detector generates an electric signal having a crest value corresponding to the detected X-ray dose, and performs signal processing such as A/D conversion on this electric signal. The A/D converted electrical signal is referred to as projection data or X-ray image data. The projection data or X-ray image data is a type of medical image data.

According to the present embodiment, medical raw data is not limited to original raw data collected by the medical image diagnostic apparatus. For example, medical raw data may be computational medical raw data that is generated by performing inverse conversion processing on medical image data. When medical raw data is collected by the CT apparatus, the inverse conversion processing corresponds to, e.g., forward projection processing. When medical raw data is collected by the MRI apparatus, the inverse conversion processing corresponds to, e.g., Fourier transformation processing.

FIG. 1 is a diagram showing a configuration of a medical data processing apparatus 1 according to a present embodiment. The medical data processing apparatus 1 shown in FIG. 1 is a computer included in the medical image diagnostic apparatus or a computer separated from the medical image diagnostic apparatus.

As shown in FIG. 1, the medical data processing apparatus 1 includes processing circuitry 11, a communication interface 12, a display 13, an input interface 14, and a memory circuitry 15.

The processing circuitry 11 includes a processor such as a CPU or GPU. By activating various programs installed in the memory circuitry 15, etc., the processor implements an obtaining function 111, a compression function 112, a decoding function 113, an image generation function 114, a display control function 115, etc. The functions 111 to 115 are respectively not limited to those realized by a single processing circuitry. A plurality of independent processors may be combined into processing circuitry, and each of the processors may execute the programs to realize the functions 111 to 115. The processing circuitry 11 may not necessarily implement all of the functions 111 to 115, and may lack some of them. For example, the processing circuitry 11 may lack any one of the compression function 112, the image generation function 114, and the display control function 115.

By implementing the obtaining function 111, the processing circuitry 11 obtains medical data. For example, the processing circuitry 11 obtains as medical data medical raw datasets acquired by the medical image diagnostic apparatus. Medical raw datasets may be obtained by way of the communication interface 12, a portable storage medium, etc., or may be obtained from the memory circuitry 15 that stores medical raw datasets received by way of the communication interface 12, a portable storage medium, etc. The processing circuitry 11 may obtain a compressed dataset generated by the compression function 112. The processing circuitry 11 may obtain a compressed dataset from other computers such as a medical image diagnostic apparatus, by way of the communication interface 12, a portable storage medium, etc., or may acquire a compressed dataset generated by the apparatus 1 itself and stored in the memory circuitry 15.

More specifically, the processing circuitry 11 acquires multicomponent medical raw data that is a compression target. In other words, the processing circuitry 11 obtains a plurality of medical raw datasets respectively corresponding to a plurality of components. Physically, components correspond to acquisition processes of respective medical raw datasets that are compression targets. Medical raw datasets that are compression targets form a group of medical raw datasets that are substantially the same in terms of position to be data-acquired and are different in terms of acquisition process. Examples of a scan system for acquiring medical raw datasets respectively corresponding to components include dual energy scan, photon counting CT, and multi-channel data collection.

Dual energy scan is performed by an X-ray computed tomography apparatus or an X-ray diagnostic apparatus. Dual energy scan is a scan system in which two types of tube voltage, a low tube voltage and a high tube voltage, are alternatively switched. By dual energy scan, a projection dataset corresponding to a low tube voltage and a projection dataset corresponding to a high tube voltage are collected as medical raw datasets respectively corresponding to components.

Photon counting CT is performed by an X-ray computed tomography apparatus or an X-ray diagnostic apparatus. Photon counting CT is a scan system in which the number of X-rays is counted for each energy bin by way of a photon counting type X-ray detector of the X-ray computed tomography apparatus or X-ray diagnostic apparatus. By photon counting CT, a plurality of projection datasets respectively corresponding to a plurality of energy bins are acquisitioned as a plurality of medical raw datasets respectively corresponding to a plurality of components. For example, about 3 to 16 energy bins are provided.

Multi-channel data acquisition is performed by a magnetic resonance imaging apparatus. Multi-channel data acquisition is a data acquisition system in which k-space data is acquired by way of a plurality of receiver channels included in reception circuitry. By multi channel data acquisition, a plurality of k-space datasets respectively corresponding to a plurality of receiver channels are acquired as a plurality of medical raw datasets respectively corresponding to a plurality of components. For example, in the case of an array coil, about 4 to 64 receiver channels are mounted.

A medical per-channel raw dataset (hereinafter, simply referred to as a "medical raw dataset") corresponding to one component is an aggregate of medical raw data that is a compression target, in particular, an aggregate of medical raw data that falls within a range of data necessary for image reconstruction. For example, when medical raw data is projection data to be acquired by an X-ray computed tomography apparatus, a medical raw dataset corresponding to one component includes projection data of the number of views per rotation of a rotation frame. When medical raw data is k-space data to be acquired by a magnetic resonance imaging apparatus, a medical raw dataset corresponding to one component includes k-space data corresponding to the number and/or a range of acquisition lines necessary for filling up one k-space.

A medical raw dataset may be further divided. In the case of using an X-ray computed tomography apparatus, a medical raw dataset may be classified as an aggregate of projection data corresponding to a predetermined number of rows instead of all rows in an X-ray detector. In the case of using a magnetic resonance imaging apparatus, a medical raw dataset may be classified as an aggregate of k-space data corresponding to blocks equal to the integral multiple of the number of times that read-out gradient magnetic field is applied, in other words, the number of echo trains, for each block of pulse sequences with blocks such as fast field echo (FFE) or fast spin echo (FSE).

By implementing the compression function 112, the processing circuitry 11 generates a compressed dataset obtained by compressing a plurality of medical raw datasets defined by a first domain representation and respectively corresponding to a plurality of components, by way of an intermediate dataset defined by a second domain representation. More specifically, the processing circuitry 11 generates an intermediate dataset by performing base conversion on a plurality of medical raw datasets respectively corresponding to a plurality of components, thereby generating a compressed dataset by performing quantization and entropy coding on the generated intermediate dataset. Conversion from medical raw datasets respectively corresponding to components to an intermediate dataset is performed by means of base conversion.

By implementing the decoding function 113, the processing circuitry 11 decodes the compressed dataset to a medical raw dataset (hereinafter referred to as a decoded medical raw dataset) defined by the first domain representation, based on the conversion process from the medical raw datasets to the compressed dataset. Specifically, the processing circuitry 11 generates an intermediate dataset defined by the second domain representation by applying an entropy decoder and an inverse quantization algorithm to a compressed dataset, thereby generating a decoded medical raw dataset by performing inverse base conversion on the generated intermediate dataset.

By implementing the image generation function 114, the processing circuitry 11 generates medical image data based on a decoded medical raw dataset. More specifically, the processing circuitry 11 generates medical image data by performing reconstruction processing on a decoded medical raw dataset. Examples of a reconstruction method include an analytical image reconstruction method and an iterative approximation reconstruction method. Examples of the analytical image reconstruction method for CT image reconstruction include a filtered back projection (FBP) method, a convolution back projection (CBP) method, and their applications. Examples of the analytical image reconstruction method for MR image reconstruction include Fourier transformation, inverse Fourier transformation, and their applications. Examples of the iterative approximation reconstruction method include an expectation maximization (EM) method, an algebraic reconstruction technique (ART) method, and their applications. Examples of the iterative approximation reconstruction method may include the above methods in combination with an analytical image reconstruction method such as FBP or Fourier transformation, or the above methods incorporating noise reduction based on a statistical model, a scanner model, an anatomical model, and/or machine learning.

By implementing the display control function 115, the processing circuitry 11 displays by way of the display 13 medical image data generated by the image generation function 114. In this implementation, the processing circuitry 11 may perform any image display processing such as gradation processing or scaling on medical image data. When medical image data generated with the image generation function 114 is three-dimensional image data, the processing circuitry 11 may convert the medical image data into two-dimensional image data by performing three-dimensional image processing thereon. As three-dimensional image processing, the processing circuitry 11 may perform volume rendering, surface volume rendering, pixel value projection processing, multi-planer reconstruction (MPR) processing, curved MPR (CPR) processing, etc.

The communication interface 12 is an interface for data communication with the medical image diagnostic apparatus or with other computers.

The display 13 displays various kinds of information in accordance with the display control function 115 of the processing circuitry 11. As the display 13, a liquid crystal display (LCD), a cathode ray tube (CRT) display, an organic electro luminescence display (OELD), a plasma display, or any other display may be suitably adopted. The display 13 may be a projector.

The input interface 14 receives various input operations from a user, converts the received input operations into electric signals, and outputs them to the processing circuitry 11. Specifically, the input interface 14 is coupled to input devices such as a mouse, a keyboard, a track ball, a switch, buttons, a joystick, a touch pad and a touch panel display. The input interface 14 outputs to the processing circuitry 11 the electric signals corresponding to the input operations to the input device. Furthermore, the input device connected to the input interface 14 may be an input device provided in another computer connected via a network or the like.

The memory circuitry 15 is a storage device for storing various kinds of information, such as a Read Only Memory (ROM), Random Access Memory (RAM), a Hard Disk Drive (HDD), a Solid State Drive (SSD), an integrated circuit storage device, etc. The memory circuitry 15 stores, for example, a medical raw dataset or a compressed dataset. Instead of the above storage device, the memory circuitry 15 may be a driving device for reading and writing various kinds of information from and to a portable storage medium such as a compact disc (CD), a digital versatile disc (DVD), a flash memory or the like, or a semiconductor memory device such as a RAM. Alternatively, the memory circuitry 15 may be provided in another computer connected to the medical data processing apparatus 1 via a network.

Hereinafter, an operation example of the medical data processing apparatus 1 will be described.

FIG. 2 is a diagram showing a typical flow of compression processing that the processing circuitry 11 performs on a medical raw dataset. As shown in FIG. 2, with the obtaining function 111, the processing circuitry 11 obtains a plurality of medical raw datasets D1 that respectively correspond to a plurality of components and are compression targets, in a step before the compression processing.

Upon acquisition of the medical raw datasets D1, the processing circuitry 11 performs conversion processing on the medical raw datasets D1 by implementing the compression function 112, thereby generating a compressed dataset D3. The processing circuitry 11 compresses the medical raw datasets D1 using both spatial and component correlations. More specifically, the processing circuitry 11 performs compression by reducing both redundancy of a spatial domain and redundancy between components included in the medical raw datasets D1.

Specifically, the processing circuitry 11 first generates a blend dataset D2 by performing base conversion on the medical raw datasets D1 (step SA1).

FIG. 3 is a schematic diagram showing base conversion. In FIG. 3, the medical raw datasets are projection data collected by photon counting CT. As shown in FIG. 3, for example, a medical raw dataset corresponding to component C1, a medical raw dataset corresponding to component C2, and a medical raw dataset corresponding to component C3 are acquired. Each medical raw dataset is defined by two or more dimensional space domain representation. For example, as shown in FIG. 3, when a medical raw dataset is defined by two-dimensional space domain representation, first axis x is defined in a row direction or a detector channel direction of an X-ray detector, and second axis y is defined in a view direction. When a medical raw dataset is defined by three-dimensional space domain representation, a first axis is defined in a row direction of the X-ray detector, a second axis is defined in a detector channel direction of the X-ray detector, and a third axis is defined in a view direction.

First, as shown in the middle of FIG. 3, the processing circuitry 11 arranges a plurality of medical raw datasets respectively corresponding to a plurality of components in an information space defined by the first domain representation. The first domain representation includes a space domain dimension and a component dimension. For example, in the case of a two-dimensional medical raw dataset, first axis x of the first domain representation is defined in a row direction or a detector channel direction of the X-ray detector, second axis y is defined in a view direction, and third axis z is defined in a component direction. In the case of a three-dimensional medical raw dataset, a first axis of the first domain representation is defined in a row direction of the X-detector, a second axis is defined in a detector channel direction, a third axis is defined in a view direction, and a fourth axis is defined in a component direction. In this manner, the plurality of medical raw datasets D1 are represented as three-dimensional or four-dimensional data.

Next, as shown at the bottom of FIG. 3, the processing circuitry 11 generates the single blend dataset D2 defined by the second domain representation by performing base conversion on the medical raw datasets D1 arranged in the information space defined by the first domain representation. The base conversion is processing for converting the first domain representation defined in a spatial domain direction and a component direction into the second domain representation defined in a spatial frequency direction. For example, orthogonal transform is performed as the base conversion. As the orthogonal transform, for example, any base conversion in an orthogonal relation, such as discrete cosine transform (DCT), discrete sine transform, discrete Fourier transform, discrete Hadamard transform, principle component analysis, etc., may be performed. In the following description, discrete cosine transform is performed as the orthogonal transform.

In the discrete cosine transform, first, the processing circuitry 11 divides the medical raw datasets D1 arranged in the information space into a plurality of blocks having a predetermined matrix size. Typically, each block has the same dimensions as those of the first domain representation. For example, when the first domain representation is a three-dimensional representation composed of a two-dimensional spatial domain and a one-dimensional component domain, a block has a three-dimensional configuration. In this case, an aggregate of the medical raw datasets D1 arranged in an information space is divided into three-dimensional blocks. When the first domain representation is a four-dimensional representation composed of a three-dimensional spatial domain and a one-dimensional component domain, a block has a four-dimensional configuration. In this case, an aggregate of the medical raw datasets D1 arranged in an information space is divided into four-dimensional blocks.

The processing circuitry 11 applies discrete cosine transform to each block, thereby calculating a conversion coefficient. The processing circuitry 11 generates the blend dataset D2 by arranging the calculated conversion coefficient in the information space of the second domain representation.

Conversion coefficient F (u, v, w) obtained by three-dimensional discrete cosine transform is expressed by the following expression. Herein, f (j, k, l) represents a value of a medical raw dataset in point (j, k, l) in the information space. N represents a block size.

$$F(u, v, w) = \frac{8C(u)C(v)C(w)}{N^3} \sum_{j=0}^{N-1}\sum_{k=0}^{N-1}\sum_{l=0}^{N-1} f(j, k, l)\cos\frac{(2j+1)u\pi}{2N}\cos\frac{(2k+1)v\pi}{2N}\cos\frac{(2l+1)w\pi}{2N}$$

Conversion coefficient F (u, v, w) is also referred to as a DCT coefficient. DCT coefficient F (u, v, w) is represented with a floating decimal point, and each point of a blend dataset is assigned DCT coefficient F (u, v, w). A conversion coefficient obtained by four-dimensional discrete cosine transform is expandable in accordance with the above expression.

The discrete cosine transform may be processed independently for each dimension. For example, in the case of a three-dimensional information space, one-dimensional discrete cosine transform is applied to the plurality of the medical raw datasets D1 in the order of x-dimension, y-dimension, and z-dimension. This order of x-dimension, y-dimension, and z-dimension is not a limitation. The discrete cosine transform may be performed in any order, for example, the order of z-dimension, y-dimension, and x-dimension. The same applies to the case of four-dimensional information space. Conversion coefficient F (u) obtained by one-dimensional discrete cosine transform can be expressed by the following expression.

$$F(u) = \frac{2C(u)}{N}\sum_{j=0}^{N-1} f(j)\cos\frac{(2j+1)u\pi}{2N}$$

In the medical raw datasets D1, a low frequency component is dominant. Thus, the blend dataset D2 has a tendency in which a DCT coefficient of a low frequency region has a relatively large value, while a DCT coefficient of a high frequency region is nearly zero.

After step SA1, the processing circuitry 11 performs quantization on the blend dataset D2 using the quantization table T1 (step SA3).

Figure 4:
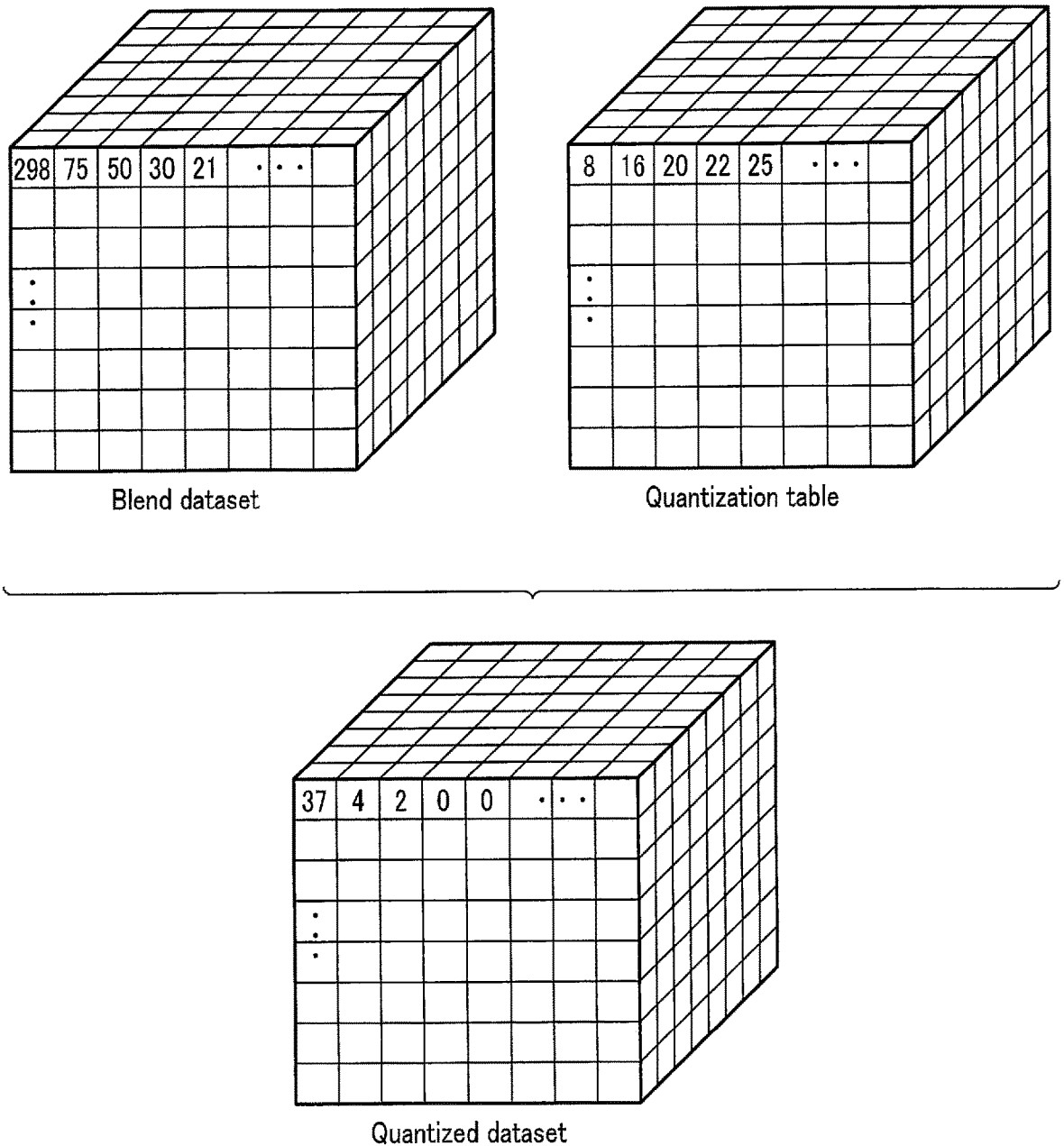
FIG. 4 is a schematic diagram showing quantization, which is illustrated in FIG. 2.

FIG. 4 is a schematic diagram showing quantization. To simplify the illustration, the blend dataset D2 and the quantization table T1 in FIG. 4 show numeric values for only the front surfaces. In each of the blend dataset D2 and the quantization table T1, the upper left direction corresponds to a low frequency region and the lower right direction corresponds to a high frequency region. Each point of the blend dataset D2 is assigned a DCT coefficient. The quantization table T1 has the same table size as that of the blend dataset D2, and has each point assigned a table value previously determined in accordance with a preset rule. For example, a point in a low frequency region, which makes a relatively high contribution to an image, is assigned a relatively small value. In contrast, a point in a high frequency region, which makes a relatively low contribution to an image, is assigned a relatively large value.

As shown in FIG. 4, the processing circuitry 11 generates a quantized dataset by applying the quantization table T1 to the blend dataset D2. Specifically, the processing circuitry 11 divides a DCT coefficient of the blend dataset D2 having the same coordinates by a table value of the quantization table T1, thereby calculating a divided value. An integer is obtained from the divided value by, for example, rounding down a fraction after the decimal point, rounding down a number less than 5 and rounding up a number equal to or larger than 5, or rounding down a number less than 5 and rounding up a number larger than 5. This integer is referred to as a quantization value. The integer processing realizes a reduced data length of quantization values at respective coordinates. Specifically in FIG. 4, see the point on the upper left end. When DCT coefficient "298" is divided by table value "8", divided value "37.25" is obtained. Then quantization value "37" is obtained by rounding down the number after the decimal point, which is less than 5. The obtained quantization value is assigned to a corresponding point in the quantized dataset. The quantized dataset is generated by performing the above processing with respect to respective points.

After step SA2, the processing circuitry 11 performs entropy coding on the quantized dataset using coding table T2 (step SA3). In this manner, compressed dataset D3 is generated. Specifically, the processing circuitry 11 first scans a three-dimensional quantized dataset along a predetermined scanning order to rearrange the dataset in a one-dimensional progression (hereinafter referred to as a quantization progression), thereby performing entropy coding on the quantization progression. The scanning order is set to a predetermined order such as a zigzag scan or raster scan.

Figure 5:
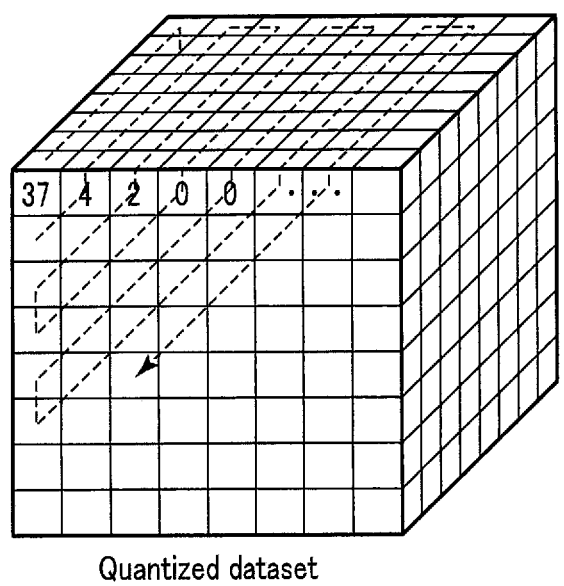
FIG. 5 is a diagram showing an example of a zigzag scan in entropy coding, which is illustrated in FIG. 2.

FIG. 5 shows an example of a zigzag scan. As shown in FIG. 5, the scanning order of a zigzag scan is determined in such a manner as to sample the quantized dataset from a low frequency region to a high frequency region. The processing circuitry 11 specifies quantization values of respective pixels in the quantized data in accordance with a scanning order of a zigzag scan, thereby rearranging the specified quantization values one-dimensionally from a starting point to an ending point of the scanning order. The zigzag scan provides a quantization progression in which quantization values are arranged in such a manner as to line up from the highest value to zero. In the quantized dataset, there is a tendency for regions other than the low frequency region to be assigned zero values. Thus, quantization values not equal to zero are arranged in the section at the beginning of the progression, whereas quantization values equal to zero are arranged in the section after the beginning. The scanning order of a zigzag scan shown in FIG. 5 is one example. The scanning order is not limited to this example and may be a scanning order for scanning strictly from a low frequency to a high frequency.

Not only a standard scanning order but also a scanning order that is freely determined may be adopted as a scanning order of a quantization dataset. For example, the processing circuitry 11 specifies quantization values of respective pixels of a given number, for example about 50, in quantized datasets, thereby determining such a scanning order that the quantization values become smaller from a starting point to an ending point. Specifically, a scanning order may be defined in accordance with a correlation between coordinates of a pixel and a sampling order of this particular pixel, and be registered in an LUT. The processing circuitry 11 reads a scanning order from the LUT, thereby generating a quantization progression by scanning a quantized dataset in accordance with the read scanning order.

There is no need to scan all the pixels in the quantized dataset. When all subsequent pixels exhibit a quantization value of zero, there is no need to scan pixels subsequent to the last non-zero pixel.

When a quantization progression is generated, the processing circuitry 11 generates compressed data by applying the quantization progression to the coding table T2. As entropy coding, Huffman coding or arithmetic compression coding is adopted. Specifically, for example, a variable length code (VLC) or a context-dependent adaptive arithmetic compression method defined by, e.g., H.264 or Joint Photographic Experts Group (JPEG) may be adopted. In the coding table T2, a content in accordance with a variable length code or a context-dependent adaptive arithmetic compression method is registered. In the case of using the variable length code, a relation between quantization values and codes is registered in the coding table T2. For example, quantization value "zero" that appears frequently is replaced with a code of a small number of digits. A one-dimensional sequence of codes obtained in this manner is a compressed dataset. In the case of using the context-dependent adaptive arithmetic compression method, a context is set in such a manner as to inherit a value of a block physically adjacent to a block that is a processing target.

A compressed dataset may be correlated with attendant information regarding a compression method. The attendant information is used to decode a medical raw dataset from a compressed dataset in decoding processing. Examples of the attendant information may include a type of base conversion, a type of quantization processing, a type of entropy coding, a quantization table, a coding table, etc. A compressed dataset may be stored in the memory circuitry 15, or may be transferred by the communication interface 12, etc., to any other computer and stored therein.

In this manner, the compression processing performed on a medical raw dataset by the processing circuitry 11 is completed.

According to the above compression processing, a plurality of medical raw datasets that are defined by two or more dimensional domain representations and respectively correspond to a plurality of components can be converted into a compressed dataset that is a one-dimensional code sequence. As described above, a plurality of medical raw datasets respectively corresponding to a plurality of components form a group of data pieces that are physically and substantially the same in terms of imaging target and are different in terms of collection process, and each component corresponds to a collection process. That is, there is a tendency for various medical raw datasets that respectively correspond to various components to be highly similar to each other in terms of space distribution. In a compression process, the plurality of medical raw datasets are collectively subjected to base conversion, thereby being converted into a blend dataset. Thereafter, quantization and entropy coding are performed on the blend dataset. Not only a spatial dimension but also a component dimension is subjected to base conversion. This enables highly efficient compression using not only redundancy of a spatial dimension but also redundancy of a component dimension.

The above-described processing is based on the premise that medical raw datasets respectively corresponding to all components collected by the medical image diagnostic apparatus are converted into a compressed dataset. However, the present embodiment is not limited to this. In medical raw datasets respectively corresponding to all components collected by the medical image diagnostic apparatus, for example, medical raw datasets corresponding to at least two or more components may be converted. For example, steps SA1 to SA3 may be performed on only a component that is a compression target selected by a user by way of the input interface 14 in a step before step SA1, so that only a medical raw dataset corresponding to the component that is the compression target may be converted into a compressed dataset.

The compression processing described above may adopt any method by which a compressed dataset can be generated from a plurality of medical raw datasets respectively corresponding to a plurality of components. Various modifications can made to the compression processing. Hereinafter, a modification of compression processing will be described.

Base conversion SA1 in the above compression processing may be performed through machine learning using a trained neural network (hereinafter referred to as a trained model). In many cases, conversion obtained through machine learning is non-linear conversion. However, in this embodiment, non-liner conversion is also referred to as base conversion for the sake of simplicity. A trained model includes a parameterized synthesis function defined by a combination of a plurality of adjustable functions and parameters (a weighting matrix or bias). A network configuration of a trained model may be realized by a multi-layer network (Deep Neural Network: DNN) having an input layer, an intermediate layer, and an output layer. A trained model may be mounted as a program or may be physically mounted on a processor such as an ASIC.

Figure 6:
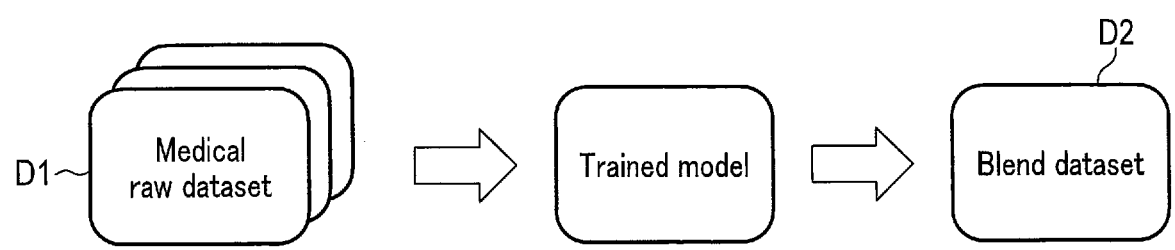
FIG. 6 is a schematic diagram showing a relationship between input and output of a trained model for compression.

FIG. 6 is a schematic diagram showing a relationship between input and output of a trained model. As shown in FIG. 6, a trained model corresponds to a neural network that is trained in such a manner that the medical raw datasets D1 respectively corresponding to components are input and a blend dataset D2 corresponding to the medical raw datasets is output. As a type of a trained model, for example, a convolutional neural network (CNN) is preferable.

A trained model may be generated by the medical data processing apparatus 1 or may be generated by any of other computers. Hereinafter, a computer having a processor such as a CPU, a GPU, etc., for generating a trained model will be referred to as a model learning apparatus. The model learning apparatus generates a trained model by causing a neural network to perform machine learning based on training data including a plurality of training samples. As a training sample, for example, the same data is prepared for both input and output. The model learning apparatus performs training by adding random noise with respect to input and inputting it to an auto encoder network that is a combination of an encoder network and a decoder network. The encoder network outputs a blend dataset. The decoder network outputs original data from the blend dataset. In the encoder network, output data is set to be lower in amount than the original data. By training the auto encoder network based on input and output data described above, a trained model is generated from the encoder network. The trained model is configured in such a manner that medical raw datasets respectively corresponding to components are input and a blend dataset is output.

Another method uses a training sample that is a combination of medical raw datasets serving as input data and respectively corresponding to components, and a blend dataset serving as supervisory data and corresponding to the medical raw datasets. The blend dataset serving as supervisory data (hereinafter referred to as a supervisory blend dataset) is explicitly given and orthogonal transform is performed on medical raw datasets respectively corresponding to components. A trained model may be generated by this method, too. The model learning apparatus performs forward propagation by applying a neural network to medical raw datasets respectively corresponding to components, thereby outputting a blend dataset (hereinafter referred to as an estimated blend dataset). Next, the model learning apparatus performs back propagation processing by applying a difference (error) between the estimated blend dataset and the supervisory blend dataset to the neural network, and calculates a gradient vector. Subsequently, the model learning apparatus updates parameters of the neural network, such as a weighted matrix and a bias, etc., based on the gradient vector. A trained model is generated by repeating the forward propagation processing, the back propagation processing, and the parameter update processing, while changing learning samples.

A trained model may be generated and stored for each imaging body part of a subject. An imaging body part may be any anatomical region such as a head, a chest, an abdomen, an inferior limb, a heart, a lung, a liver, etc. A trained model for each imaging body part may be generated by training a neural network through machine learning based on a training sample relating to a single imaging body part. A trained model for each imaging body part is stored in the memory circuitry 15 in such a manner that each imaging body part is correlated with information thereon.

Figure 7:
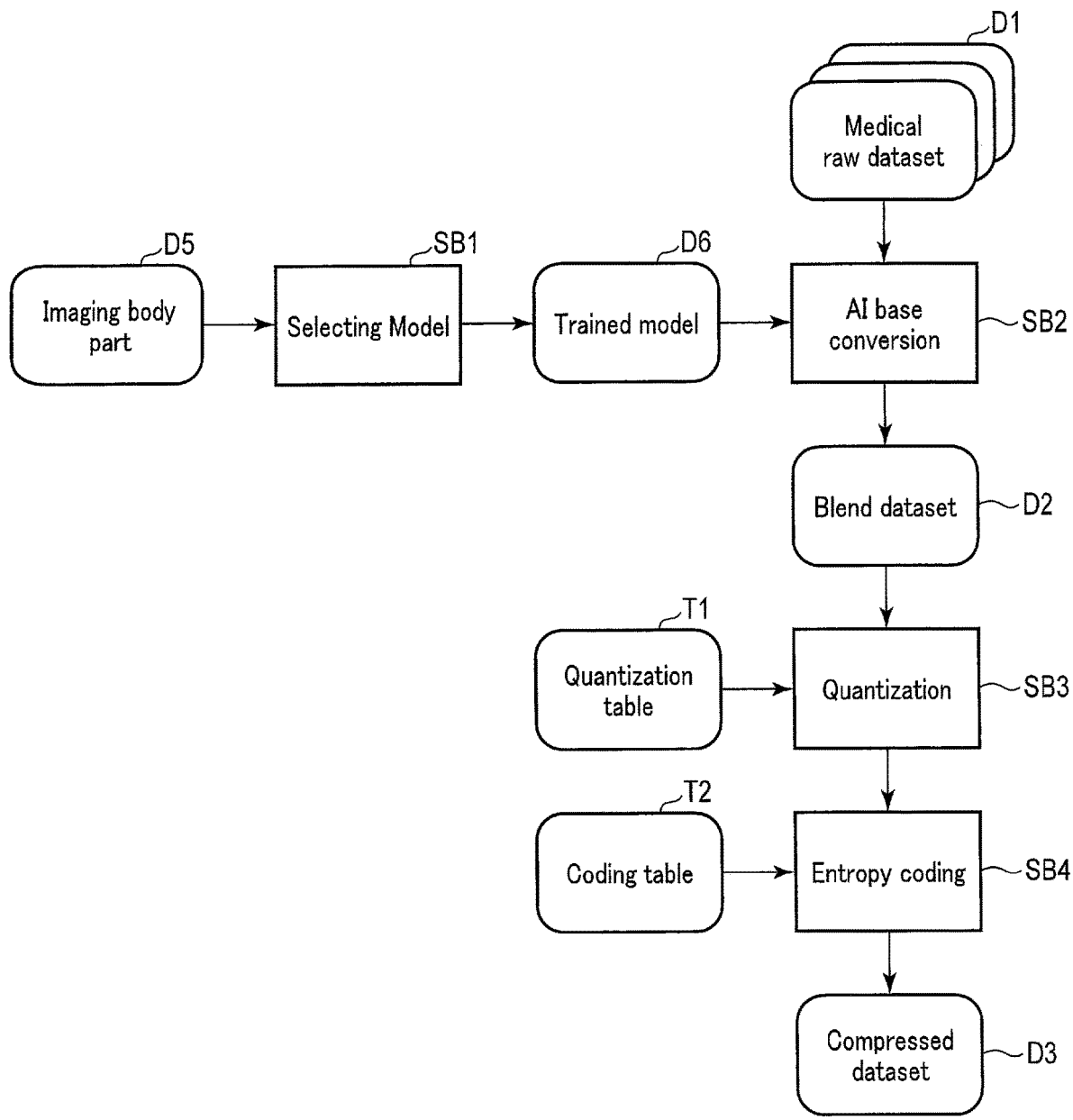
FIG. 7 is a diagram showing a typical flow of compression processing that processing circuitry 11 performs on medical raw datasets when a trained model for compression is generated and stored for each imaging body part.

FIG. 7 is a diagram showing a typical flow of compression processing that processing circuitry 11 performs on medical raw datasets when a trained model for compression is generated and stored for each imaging body part. As shown in FIG. 7, with the obtaining function 111, the processing circuitry 11 obtains the medical raw datasets D1 each serving as a compression target and respectively corresponding to components, in a step before the compression processing. With the obtaining function 111, the processing circuitry 11 obtains information on an imaging body part D5 regarding a subject of the medical raw datasets D1. Information on the imaging body part D5 is correlated with, for example, the medical raw datasets D1.

When obtaining the medical raw datasets D1 and the information on the imaging body part D5, by implementing the compression function 112, the processing circuitry 11 generates a compressed dataset D3 by performing on the medical raw datasets D1 conversion processing that involves base conversion by machine learning (hereinafter referred to as AI base conversion).

First, with the compression function 112, the processing circuitry 11 selects a trained model D6 correlated with the imaging body part D5 (step SB1). In step SB1, specifically, the processing circuitry 11 selects a trained model correlated with the imaging body part D5 from a plurality of trained models stored in the memory circuitry 15, and reads the selected trained model.

In some cases, trained models that are different in terms of imaging body part D5 are the same in terms of network configuration and different in terms of parameter set. In such a case, information on the imaging body part D5 may be stored in the memory circuitry 15 in such a manner that the information is correlated with a parameter set. In step SB1, the processing circuitry 11 selects a parameter set correlated with the imaging body part D5 from a plurality of parameter sets stored in the memory circuitry 15, and reads the selected parameter set. The processing circuitry 11 sets the read parameter set to a neural network. In this manner, a trained model is selected.

After step SB1, the processing circuitry 11 executes AI base conversion (step SB2). Specifically, the processing circuitry 11 generates the blend dataset D2 by applying the trained model D6 selected in step SB1 to the medical raw datasets D1.

After step SB2, the processing circuitry 11 generates the compressed dataset D3 by performing quantization on the blend dataset D2 using the quantization table T1 (step SB3), and then performing entropy coding on the quantized data using the coding table T2 (step SB4), thereby generating the compressed dataset D3. Step SB3 is the same as step SA2 in FIG. 2. Step SB4 is the same as step SA3 in FIG. 2.

When AI base conversion is executed, the quantization table T1 may be changed for each collection process of a medical raw dataset. Hereinafter, this implementation example will be described by using as an example a case in which medical raw datasets are projection datasets collected by a dual energy scan with an X-ray computed tomography apparatus. The following description assumes that medical raw datasets are grouped for respective X-ray detector channels.

Figure 8:
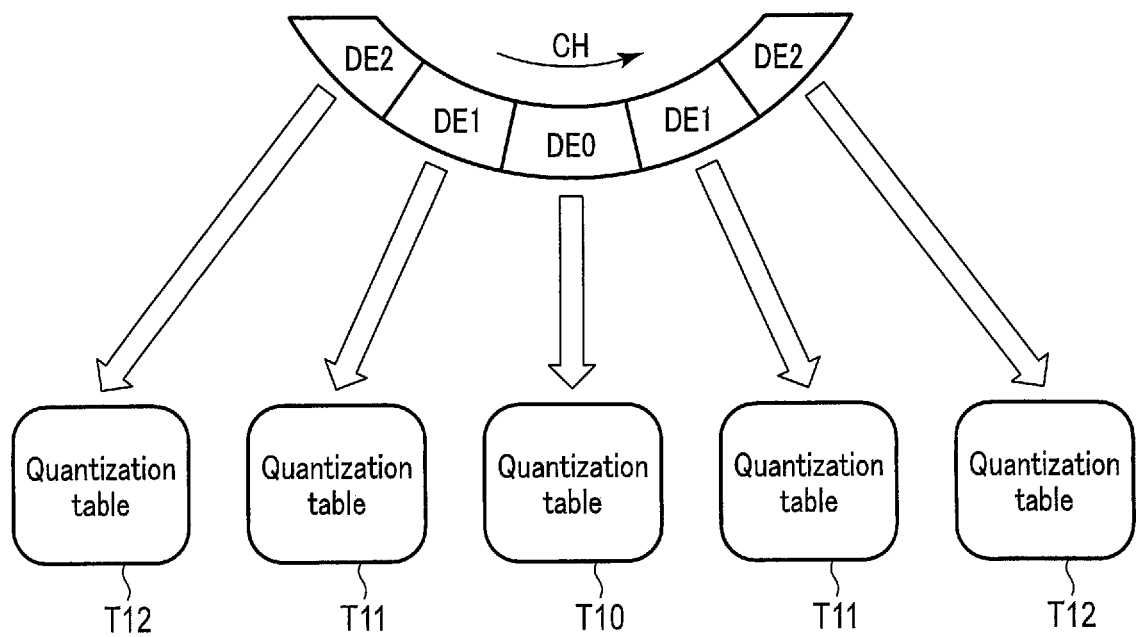
FIG. 8 is a diagram showing a correspondence relationship between groups of X-ray detector channels and quantization tables.

FIG. 8 is a diagram showing a correspondence relationship between groups of X-ray detector channels and quantization tables. As shown in FIG. 8, for example, the X-ray detector channels are grouped into a center part DE0, intermediate parts DE1, and edge parts DE2 in a channel direction CH. Tables prepared in this case are a quantization table T10 corresponding to the center part DE0, a quantization table T11 corresponding to the intermediate parts DE1, and a quantization table T12 corresponding to the edge parts DE2. A blend dataset is generated based on a projection dataset of the center part DE0. A blend dataset is generated based on a projection dataset of each intermediate part DE1. A blend dataset is generated based on a projection dataset of each edge part DE2. The edge parts DE2 have a tendency to detect direct X-rays that do not pass through a subject. Projection datasets acquired in the edge parts DE2 tend to make little contribution to an image. Thus, table values in the quantization table T12 are preferably set to be relatively large. On the other hand, the center part DE0 and the intermediate parts DE1 have a tendency to detect X-rays that passed through a subject. Projection datasets acquired in the center part DE0 and the intermediate parts DE1 tend to contribute to an image. Thus, table values in the quantization tables T10 and T11 are preferably set to be relatively small. In particular, since projection datasets acquired in the center part DE0 tend to make a large contribution to an image, table values in the quantization table T10 are set to be smaller than those in the quantization tables T11 and T12.

The optimum compression efficiency can be achieved in accordance with a physical position of a medical raw dataset by changing the quantization table T1 in accordance with the physical position of the medical raw dataset.

The above-described implementation example is premised on the trained model in which medical raw datasets serving as input and a blend dataset serving as output are equal in terms of number of components. However, the present embodiment is not limited to this. Hereinafter, this implementation example will be described by using as an example a case in which medical raw datasets are projection datasets collected by photon counting CT with an X-ray computed tomography apparatus.

Figure 9:
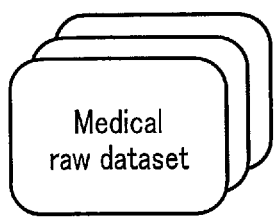
FIG. 9 is a diagram showing a relationship between input and output of a trained model for compression, which differs in number of components between input and output.
Figure 9:
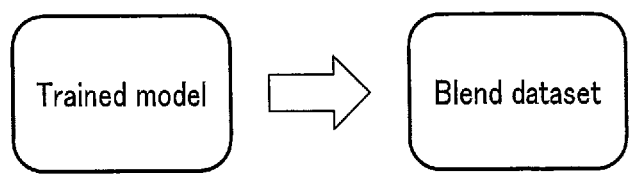

FIG. 9 is a diagram showing a relationship between input and output of a trained model in which input and output differ in number of components. In the trained model shown in FIG. 9, output is set to be smaller in number of components than input. Photon counting CT collects a projection dataset for each energy bin; however, projection datasets for all energy bins are not always necessary. For example, assume that three energy bins are prepared. The first energy bin is for discriminating an X-ray photon that passed through water. The second energy bin is for discriminating an X-ray photon that passed through a bone. The third energy bin is for discriminating noise. A projection dataset for the third energy bin for discriminating noise may not be compressed because it is not necessary for imaging. In the first to the third energy bins, projection datasets for the first and second energy bins are converted into a blend dataset, whereas a projection dataset for the third energy bin is not converted into the blend dataset. This further increases compression efficiency.

A trained model shown in FIG. 9 corresponds to a neural network that is trained in such a manner that the first, second, and third medical raw datasets respectively corresponding to the first, second, and third components are input and a blend dataset corresponding to the first and second medical raw datasets is output. A training sample is a combination of the first, second, and third medical raw datasets each serving as input data and a blend dataset serving as supervisory data and corresponding to the first and second medical raw datasets. The blend dataset that is supervisory data is generated by performing orthogonal transform on the first and second medical raw datasets.

Next, the decoding processing with the decoding function 113 of the processing circuitry 11 will be described.

FIG. 10 is a diagram showing a typical flow of decoding processing that the processing circuitry shown in FIG. 1 performs on a compressed dataset. In a step before the decoding processing, with the obtaining function ill, the processing circuitry 11 obtains the compressed dataset D3 that is a compression target.

Upon acquisition of the compressed dataset D3, by implementing the decoding function 113, the processing circuitry 11 performs the decoding processing on the compressed dataset D3, thereby decoding it to a plurality of medical raw datasets D8 respectively corresponding to a plurality of components. The decoding processing is performed by retrograding a conversion process (compression process) from the plurality of medical raw datasets D1 respectively corresponding to the plurality of components to the compressed dataset D3. Hereinafter, a medical raw dataset obtained by decoding will be referred to as a decoded medical raw dataset.

Specifically, the processing circuitry 11 performs entropy decoding on the compressed dataset D3 using the coding table T3 (step SC1). In step SC1, the processing circuitry 11 performs entropy decoding by referring to attendant information regarding a compression method, which is associated with the compressed dataset D3. A quantization progression is generated by entropy decoding.

After SC1, the processing circuitry 11 performs inverse quantization on the quantization progression using a quantization table T4 (step SC2). In step SC2, the processing circuitry 11 performs inverse quantization by referring to attendant information regarding a compression method, which is associated with the compressed dataset D3. By the inverse quantization, a blend dataset D7 is generated.

After step SC2, the processing circuitry 11 performs inverse base conversion on the blend dataset D7, thereby generating a decoded medical raw dataset D8 (step SC3). For example, the processing circuitry 11 decodes the blend dataset D7 to the decoded medical raw datasets D8 corresponding to all the components taken in the compressed dataset D3. Furthermore, the processing circuitry 11 may decode the blend dataset D7 to the decoded medical raw dataset D8 corresponding to only components freely selected from all the components incorporated into the compressed dataset D3. For example, the processing circuitry 11 may decode the blend dataset D7 to the decoded medical raw dataset D8 corresponding to only a component serving as an imaging target and selected by a user by way of the input interface 14.

The inverse base conversion is inverse conversion of base conversion from the medical raw datasets D1 respectively corresponding to components to the blend dataset D2. For example, if orthogonal transform is performed as base conversion to the blend dataset D2, inverse orthogonal conversion is performed as inverse base conversion. More specifically, if discrete cosine transform is performed as orthogonal transform, inverse discrete cosine transform is performed as inverse orthogonal transform.

Inverse conversion coefficient f (j, k, l) obtained by three-dimensional inverse discrete cosine transform is expressed by the following expression. Herein, F (u, v, w) is a value of a blend dataset in point (u, v, w) in a spatial frequency space. N represents a size of block. In the case of four-dimensional spatial frequency space, the following expression may be four-dimensionally expanded.

$$f(j,k,l) = \frac{8C(u)C(v)C(w)}{N^3}$$

$$\sum_{j=0}^{N-1}\sum_{k=0}^{N-1}\sum_{l=0}^{N-1} F(u,v,w)\cos\frac{(2j+1)u\pi}{2N}\cos\frac{(2k+1)v\pi}{2N}\cos\frac{(2l+1)w\pi}{2N}$$

Inverse discrete cosine transform may be processed independently for each dimension, as in discrete cosine transform. For example, in the case of a three-dimensional spatial frequency space, one-dimensional inverse discrete cosine transform is applied to the blend dataset D7 in the order of fx-dimension, fy-dimension, and fz-dimension. This order of gx-dimension, gy-dimension, and gz-dimension is not a limitation. The inverse discrete cosine transform may be performed in any order, for example, the order of fz-dimension, fy-dimension, and fx-dimension. The same applies to the case of a four-dimensional spatial frequency space. Inverse conversion coefficient f (j) obtained by one-dimensional inverse discrete cosine transform can be expressed by the following expression.

$$f(j) = \frac{2C(u)}{N}\sum_{j=0}^{N-1} F(u)\cos\frac{(2j+1)u\pi}{2N}$$

In this manner, the decoding processing that the processing circuitry 11 performs on a compressed dataset is completed. Thereafter, medical image data is generated based on the decoded medical raw dataset, is subjected to appropriate image processing, and is displayed on the display 13.

According to the above decoding processing, a compressed dataset that is a one-dimensional code sequence generated by the compression processing described above can be decoded by utilizing a conversion process in the compressed processing to a plurality of decoded medical raw datasets that are defined by two or more dimensional domain representation and respectively correspond to a plurality of components. The compressed dataset is data compressed with a high efficiency in terms of both spatial dimension and a component dimension. Thus, the compressed data can be decoded with a high efficiency in terms of both a spatial dimension and a component dimension through the decoding processing utilizing a conversion process in the compression processing described above.

The decoding processing described above may adopt any method by which a decoded medical raw dataset can be generated from a compressed dataset. Various modifications can be made to the decoding processing. Hereinafter, a modification of decoding processing will be described.

Inverse base conversion SC3 in the above decoding processing may be performed through machine learning using a trained model.

FIG. 11 is a schematic diagram showing a relationship between input and output of a trained model for decoding processing. As shown in FIG. 11, a trained model corresponds to a neural network that is trained in such a manner that a blend dataset is input and medical raw datasets respectively corresponding to components corresponding to the compressed dataset is output.

A trained model is generated by a model learning apparatus. The model learning apparatus generates a trained model by causing a neural network to perform machine learning based on training data including a plurality of training samples. As a training sample, for example, the same data is prepared for both input and output. The model learning apparatus performs learning by adding random noise with respect to input and inputting it to an auto encoder network that is a combination of an encoder network and a decoder network. The encoder network outputs a blend dataset. The decoder network outputs original data from the blend dataset. In the encoder network, output data is set to be lower in amount than original data. By training the auto encoder network based on input and output data described above, a trained model is generated from the encoder network. The trained model is configured in such a manner that a blend dataset is input and decoded medical raw datasets respectively corresponding to components are output.

Another method uses a training sample that is a combination of a blend dataset serving as input data and decoded medical raw datasets respectively corresponding to components corresponding to the blend dataset serving as supervisory data. The decoded medical raw datasets serving a supervisory data (hereinafter referred to as supervisory decoded medical raw datasets) are explicitly given and inverse orthogonal transform is performed on the blend dataset. A trained model may be generated by this method, too. The model learning apparatus performs forward propagation by applying a neural network to a blend dataset, thereby outputting medical raw datasets respectively corresponding to components (hereinafter referred to as estimated decoded medical raw datasets). Next, the model learning apparatus performs back propagation processing by applying a difference (error) between the estimated decoded medical raw dataset and the supervisory decoded medical raw dataset to the neural network, and calculates a gradient vector. Subsequently, the model learning apparatus updates parameters of the neural network based on the gradient vector. A trained model is generated by repeating the forward propagation processing, the back propagation processing, and the parameter update processing, while changing learning samples.

As in a trained model for compression, a trained model for decoding may be generated and stored for each imaging body part of a subject. A trained model for decoding for each imaging body part may be generated by training a neural network through machine learning based on a training sample regarding a single imaging body part. A trained model for compression for each imaging body part is stored in the memory circuitry 15 in such a manner that each imaging body part is correlated with information thereon.

Figure 12:
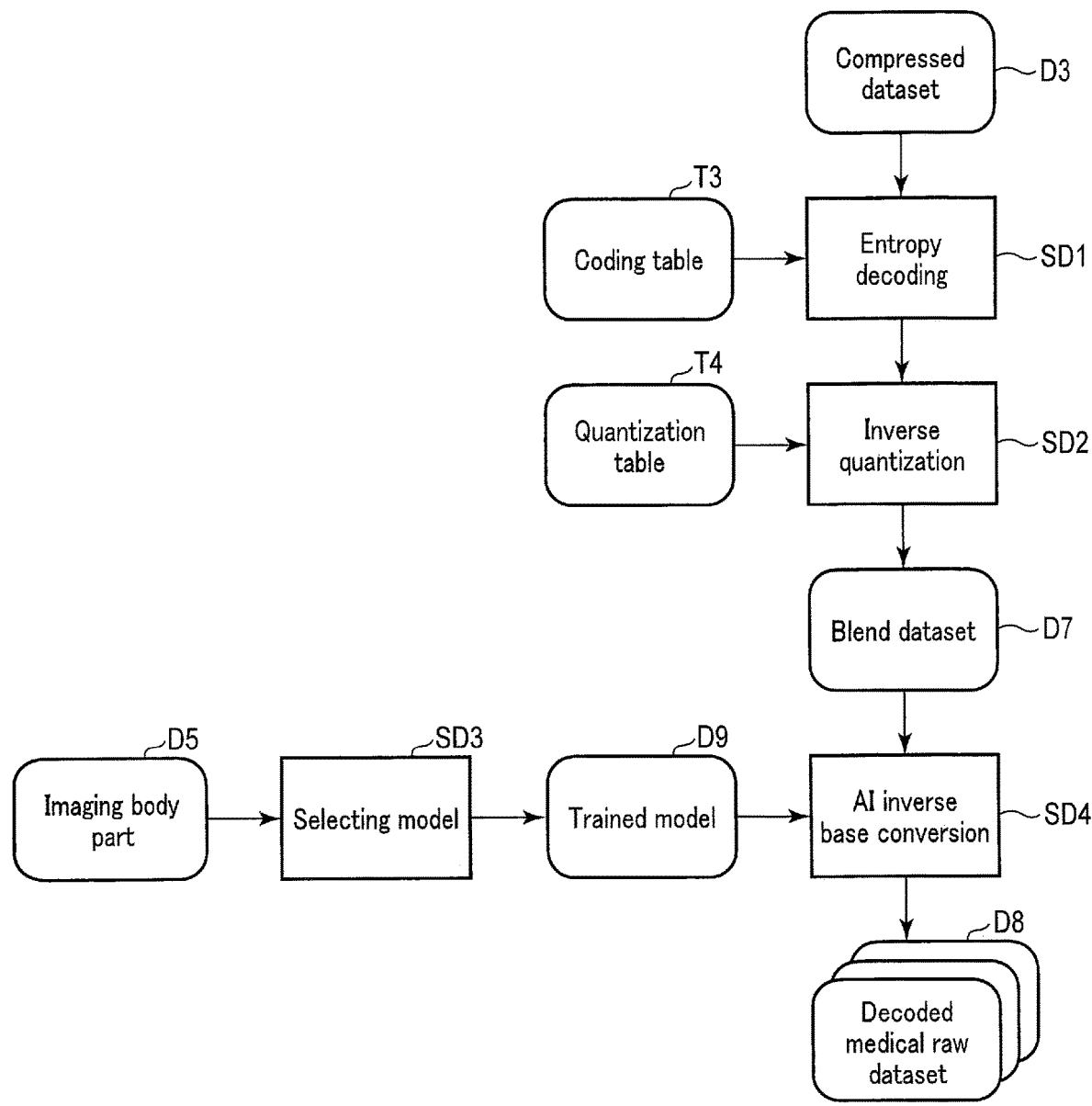
FIG. 12 is a diagram showing a typical flow of decoding processing that processing circuitry performs on a compressed dataset when a trained model for decoding is generated and stored for each imaging body part.

FIG. 12 is a diagram showing a typical flow of decoding processing that the processing circuitry 11 performs on a compressed dataset when a trained model for decoding is generated and stored for each imaging body part. As shown in FIG. 12, in a step before the decoding processing, with the obtaining function 111, the processing circuitry 11 obtains a compressed dataset D3 that is a compression target. With the obtaining function 111, the processing circuitry 11 obtains information on an imaging body part D5 regarding a subject of a compressed dataset.

When obtaining the compressed dataset D3 and the information on the imaging body part D5, by implementing the decoding function 113, the processing circuitry 11 generates a plurality of decoded medical raw datasets D8 by performing on the compressed dataset D3 inverse conversion processing that involves inverse base conversion by machine learning (hereinafter referred to as AI inverse base conversion).

First, the processing circuitry 11 performs entropy decoding on the compressed dataset D3 using the coding table T3 (step SD1) and performs inverse quantization on a quantization progression using a quantization table T4 (step SD2), thereby generating the blend dataset D7. Step SD1 is the same as step SC1 in FIG. 10. Step SD2 is the same as step SC2 in FIG. 10.

On the other hand, with the decoding function 113, the processing circuitry 11 selects a trained model D9 for decompression correlated with the imaging body part D5 (step SD3). In step SD3, the processing circuitry 11 selects a trained model for decoding correlated with the imaging body part D5 from a plurality of trained models for decoding stored in the memory circuitry 15, and reads the selected trained model for decoding.

In some cases, trained models that are different in terms of imaging body part D5 are the same in terms of network configuration and different in terms of parameter set. In such a case, information on the imaging body part D5 may be stored in the memory circuitry 15 in such a manner that the information is correlated with a parameter set. In step SD3, the processing circuitry 11 selects a parameter set correlated with the imaging body part D5 from a plurality of parameter sets stored in the memory circuitry 15, and reads the selected parameter set. The processing circuitry 11 sets the read parameter set to a neural network for decoding. In this manner, a trained model for decoding is selected.

After steps SD2 and SD3, the processing circuitry 11 executes AI inverse base conversion (step SD4). Specifically, the processing circuitry 11 generates a plurality of medical raw datasets D8 respectively corresponding to a plurality of components by applying a trained model D9 for decoding selected in step SD3 to the blend dataset D7.

In this manner, the decoding processing utilizing AI inverse base conversion is completed. Step SD3 may be performed any time before SD4 is performed. That is, step SD3 may be performed prior to step SD1 or step SD2.

The above-described implementation example is premised on the trained model in which a blend dataset serving as input and decoded medical raw datasets serving as output are equal in terms of number of components. However, the present embodiment is not limited to this. Hereinafter, this implementation example will be described by using as an example a case in which medical raw datasets are projection datasets collected by photon counting CT with an X-ray computed tomography apparatus.

Figure 13:
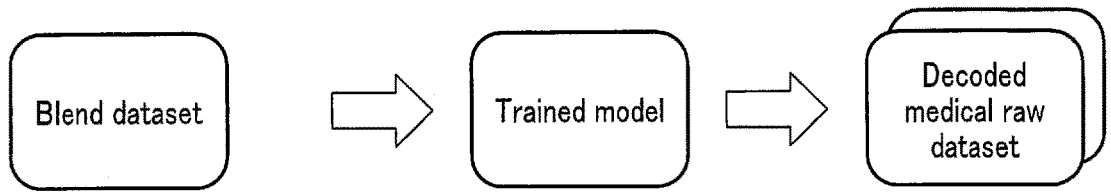
FIG. 13 is a diagram showing a relationship between input and output of a trained model for decoding that differs in number of components between input and output.

FIG. 13 is a diagram showing a relationship between input and output of a trained model for decoding that differs in number of components between input and output. In the trained model shown in FIG. 13, output is set to be smaller in number of components than input. Photon counting CT collects a projection dataset for each energy bin; however, projection datasets for all energy bins are not always necessary. For example, assume that three energy bins are prepared. The first energy bin is for discriminating an X-ray photon that passed through water. The second energy bin is for discriminating an X-ray photon that passed through a bone. The third energy bin is for discriminating noise. A projection dataset for the third energy bin for discriminating noise may not be decoded because it is not necessary for imaging. In the first to the third energy bins, projection datasets of the first and second energy bins are decoded, whereas a projection dataset of the third energy bin is not decoded. This further increases compression efficiency.

A trained model shown in FIG. 13 corresponds to a neural network that is trained in such a manner that a blend dataset corresponding to the first, second, and third components is input and the first and second medical raw datasets respectively corresponding to the first and second components are output. A training sample is a combination of the blend dataset serving as input data and relating to the first, second, and third medical raw datasets and the first and second medical raw datasets serving as supervisory data. The first and second medical raw datasets that are supervisory data may be generated and extracted by performing orthogonal transform on the first, second, and third blend datasets, or may be the original first and second medical raw datasets.

The above example was described based on the premise that the number of components on the output side is smaller by one than the number of components on the input side. However, the present embodiment is not limited to this. For example, the number of components on the output side may be smaller by two than the number of components on the input side, or may be one regardless of the number of components on the input side.

As described above, the medical data processing apparatus 1 includes the processing circuitry 11. The processing circuitry 11 implements at least the obtaining function 111 and the decoding function 113. By implementing the obtaining function 111, the processing circuitry 11 obtains a compressed dataset obtained by compressing a plurality of first medical datasets defined by the first domain representation including a spatial domain dimension and a component dimension and respectively corresponding to a plurality of components, by way of an intermediate dataset defined by the second domain representation including a frequency dimension. By implementing the decoding function 113, the processing circuitry 11 decodes the compressed dataset to the second medical dataset defined by the first domain representation based on a conversion process from the plurality of first medical datasets to the compressed dataset.

The above structure utilizes not only a spatial correlation but also a component correlation, and thus enables a plurality of medical datasets respectively corresponding to a plurality of components to be compressed with a high efficiency by reducing both redundancy of a spatial domain and redundancy between components. Accordingly, the medical datasets can be compressed with a high efficiency. In addition, the medical datasets can be decoded from the compressed dataset with a high efficiency based on the compression process described above.

(First Modification)

The medical data processing apparatus 1 shown in FIG. 1 is configured in such a manner that the processing circuitry 11 having both the compression function 112 and the decoding function 113 is mounted on the medical data processing apparatus 1. However, the compression function 112 and the decoding function 113 may be dispersed and mounted on separate hardware devices. Hereinafter, a first modification will be described. In the description below, structural elements having substantially the same functions as those in the present embodiment will be denoted by the same reference symbols, and repeat descriptions of such elements will be given only where necessary.

Figure 14:
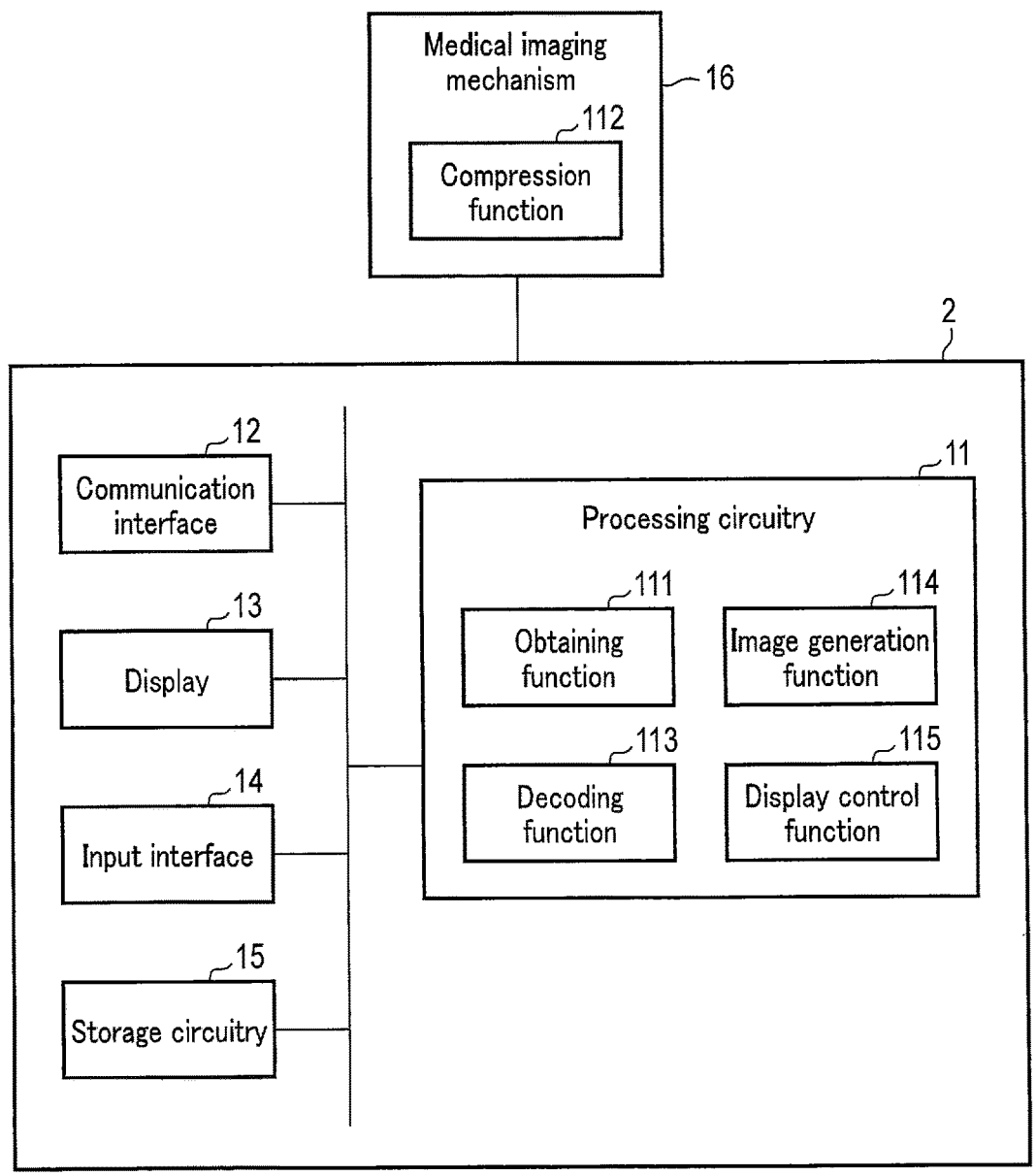
FIG. 14 is a diagram showing a configuration of a medical image diagnostic apparatus according to a first modification.

FIG. 14 is a diagram showing a configuration of a medical image diagnostic apparatus according to a first modification. As shown in FIG. 14, the medical image diagnostic apparatus according to the first modification includes a medical imaging mechanism 16 and a medical data processing apparatus 2 that are connected to each other via a cable or a network. The medical imaging mechanism 16 corresponds to an imaging mechanism for the medical image diagnostic apparatus described above. The medical data processing apparatus 2 corresponds to a console configured to control the medical imaging mechanism 16, perform image reconstruction, and so on.

The medical imaging mechanism 16 collects a plurality of medical raw datasets respectively corresponding to a plurality of components by performing medical imaging on a subject in accordance with each imaging principle. Processing circuitry of the medical imaging mechanism 16 has the compression function 112. With the compression function 112, the medical imaging mechanism 16 generates a compressed dataset based on the plurality of collected medical raw datasets. The medical imaging mechanism 16 transmits the compressed dataset to the medical data processing apparatus 2.

The medical data processing apparatus 2 includes the processing circuitry 11, the communication interface 12, the display 13, the input interface 14, and the memory circuitry 15. The processing circuitry 11 includes a processor such as a CPU or GPU. By activating various programs installed in the memory circuitry 15, etc., the processor implements the obtaining function 111, the decoding function 113, the image generation function 114, the display control function 115, etc.

By implementing the obtaining function ill, the processing circuitry 11 obtains a compressed dataset transmitted from the medical imaging mechanism 16. The processing circuitry 11 may obtain a compressed dataset directly from the medical imaging mechanism 16, by way of the communication interface 12, a portable storage medium, etc., or may obtain a compressed dataset transmitted by the medical imaging mechanism 16 and stored in the memory circuitry 15.

By implementing the decoding function 113, the processing circuitry 11 decodes the compressed dataset to a decoded medical raw dataset defined by the first domain representation based on a conversion process from the plurality of medical raw datasets to the compressed dataset.

The image generation function 114, the display control function 115, the communication interface 12, the display 13, the input interface 14, and the memory circuitry 15 are the same as those in the embodiment described above. Thus, the description for them is omitted herein.

Hereinafter, a specific example according to the first modification will be described.

When the medical imaging mechanism 16 corresponds to a gantry of an X-ray computed tomography apparatus, the processing circuitry that implements the compression function 112 is provided in a rotating unit. In the rotating unit, a plurality of projection datasets respectively corresponding to a plurality of components are converted into a compressed dataset. In the case of dual energy scan, a plurality of projection datasets respectively corresponding to a plurality of tube voltage values are converted into a compressed dataset. A compressed dataset is transferred to the medical data processing apparatus 2 by way of a fixed unit. With the decoding function 113, the compressed dataset is decoded to a plurality of decoded projection datasets respectively corresponding to a plurality of tube voltage values. With the image generation function 114, a monochromatic X-ray image, a material decomposition image, or the like is generated based on the plurality of decoded projection datasets and is displayed on the display 13.

In the case of photon counting CT, a plurality of projection datasets respectively corresponding to a plurality of energy bins are converted into a compressed dataset. A compressed dataset is transferred to the medical data processing apparatus 2 by way of a fixed unit. With the decoding function 113, the compressed dataset is decoded to a plurality of decoded projection datasets respectively corresponding to a plurality of energy bins. With the image generation function 114, a monochromatic X-ray image, a material decomposition image, or the like is generated based on the plurality of decoded projection datasets and is displayed on the display 13.

When the medical imaging mechanism 16 corresponds to a gantry of a magnetic resonance apparatus, the processing circuitry that implements the compression function 112 is provided in a reception circuitry. In the reception circuitry, a plurality of k-space datasets respectively corresponding to a plurality of receiver channels are converted into a compressed dataset. A compressed dataset is transferred to the medical data processing apparatus 2 by way of a fixed unit. With the decoding function 113, the compressed dataset is decoded to a plurality of decoded k-space datasets respectively corresponding to a plurality of tube voltage values. With the image generation function 114, an MR image is generated based on the plurality of decoded k-space datasets and is displayed on the display 13.

As described above, according to the first modification, the medical imaging mechanism 16 transmits compressed data and thus realizes a reduced amount of transmitted data as compared to the case of transmitting a plurality of medical raw datasets respectively corresponding to a plurality of components. This enables high-speed data transmission and a simplified transmission facility. The decoding function 113 mounted on the medical data processing apparatus 2 enables the medical data processing apparatus 2 to, e.g., generate and image a medical image based on a compressed dataset.

(Second Modification)

In some cases, a plurality of medical raw datasets respectively corresponding to a plurality of components are used as a training sample. Machine learning requires many training samples, and thus requires a large storage area to store training samples. In the medical data processing system according to a second modification, the compression function 112 is mounted on each medical image diagnostic apparatus that generates a training sample, and the decoding function 113 is mounted on the model learning apparatus. Hereinafter, the medical data processing system according to the second modification will be described. In the description below, structural elements having substantially the same functions as those in the present embodiment will be denoted by the same reference symbols, and a repeat description of such elements will be given only where necessary.

Figure 15:
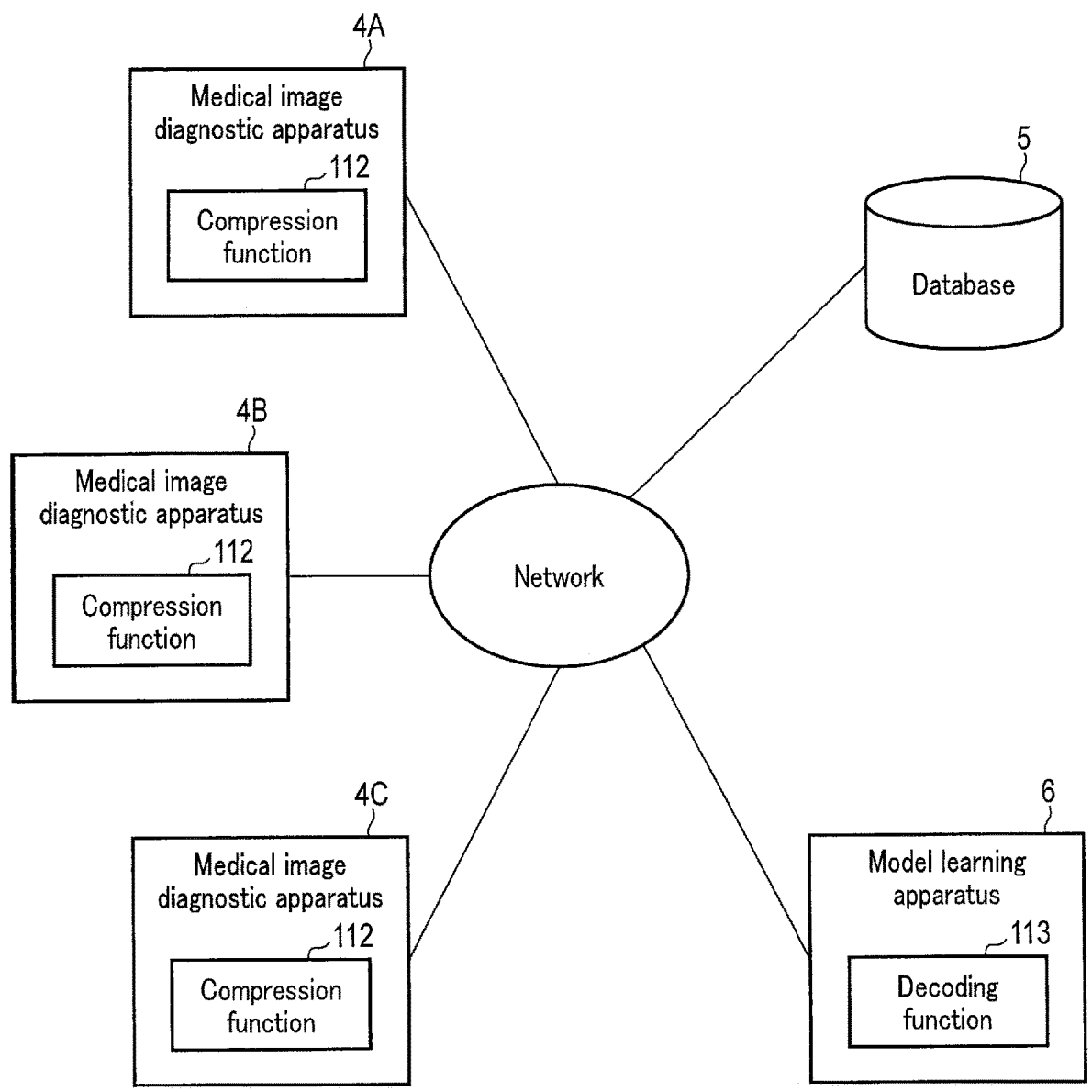
FIG. 15 is a diagram showing a configuration of a medical data processing system according to a second modification.

FIG. 15 is a diagram showing a configuration of a medical data processing system according to the second modification. As shown in FIG. 15, the medical data processing system according to the second modification includes a plurality of medical image diagnostic apparatuses 4A, 4B, and 4C, a database 5, and a model learning apparatus 6. FIG. 15 shows three medical image diagnostic apparatuses, i.e., the medical image diagnostic apparatuses 4A, 4B, and 4C. However, the number of medical image diagnostic apparatuses 4 provided in the medical data processing system is not particularly limited, and may be two or less or four or more. Hereinafter, the medical image diagnostic apparatuses 4A, 4B, and 4C will be simply and collectively referred to as the medical image diagnostic apparatus 4 without distinction between the apparatuses 4A, 4B, and 4C.

The medical image diagnostic apparatus 4 collects a plurality of datasets respectively corresponding to a plurality of components. The medical image diagnostic apparatuses may be the same or different in terms of type. By implementing the compression function 112, the medical image diagnostic apparatus 4 generates a compressed dataset by performing compression processing on a plurality of medical raw datasets. The generated compressed dataset and a plurality of medical raw datasets based on the compressed dataset are transmitted as a training sample to the database 5. A plurality of medical raw datasets contained in a training sample may be subjected to lossless compression.

The database 5 corresponds to a mass-storage device or a computer provided with the mass-storage device, which stores a training sample including a compressed dataset and medical raw datasets based on the compressed dataset, which are transmitted from the medical image diagnostic apparatus 4.

As described above, the model learning apparatus 6 corresponds to a computer that generates a trained model by causing a neural network to perform machine learning based on training data including a plurality of training samples. By implementing the decoding function 113, the model learning apparatus 6 according to the second modification decodes data to a plurality of decoded medical raw datasets respectively corresponding to a plurality of components based on a compressed dataset contained in a single training sample. The plurality of decoded medical raw datasets are utilized as supervisory data. The model learning apparatus 6 performs learning of parameters of a neural network based on the compressed dataset and the decoded medical raw datasets. The model learning apparatus 6 repeats parameter learning while changing a compressed dataset, thereby generating a trained model.

The configuration of the medical data processing system according to the second modification is not limited to the one shown in FIG. 14. For example, the database 5 may be incorporated into the model learning apparatus 6. The above description is based on the premise that the decoding function 113 is mounted on the model learning apparatus 6. However, the decoding function 113 may be mounted on a computer separated from the model learning apparatus 6. In the above description, the compression function 112 is mounted on the medical image diagnostic apparatus 4. However, the compression function 112 may be mounted on a computer different from the medical image diagnostic apparatus 4.

As described above, by providing the medical data processing system according to the second modification with the compression function 112, training samples can be compressed and stored in a case of using medical raw datasets respectively corresponding to components as training samples for machine learning. This enables a reduced storage area for training samples and a simplified storage facility. By providing the medical data processing system according to the second modification with the decoding function 113, machine learning can be performed appropriately by decoding compressed training samples.

(Third Modification)

The processing circuitry 11 according to a third modification may perform prediction between a plurality of components. When medical datasets are collected by an X-ray computed tomography apparatus, the processing circuitry 11 predicts projection datasets in units of a predetermined number of rows of an X-ray detector. In the detector, projection data is similar between adjacent rows. Thus, the prediction efficiency is high. When medical raw datasets are acquired by a magnetic resonance imaging apparatus, the processing circuitry 11 predicts k-space datasets in units of blocks equal to the integral multiple of the number of times that a read-out gradient magnetic field is applied, in other words, the number of echo trains, for each block of pulse sequences with blocks such as FFE or FSE. K-space data is similar between adjacent blocks. Thus, the prediction efficiency is high. The prediction may be performed by a method prescribed by H.264, etc., such as Intra prediction, DC prediction, etc. The prediction may be performed by a recurrent neural network (RNN). By performing the prediction, the amount of data can be further reduced. If the prediction is performed in a compression process, a similar prediction to the one in the compression process may be performed in a decoding process, too. That is, the processing circuitry 11 may predict decoded projection datasets in units of a predetermined number of rows in an X-ray detector or predict decoded k-space datasets in units of blocks equal to an integral multiple of a number of echo trains.

(Fourth Modification)

The above embodiment was described based on the premise that a plurality of medical raw data sets respectively corresponding to a plurality of components are subjected to base conversion. However, the present embodiment is not limited to this. The processing circuitry 11 may input a residual error between a plurality of medical raw datasets respectively corresponding to a plurality of components into a trained model, and output a blend dataset. Specifically, the processing circuitry 11 inputs a residual error in a medical raw dataset between two components that are physically adjacent to each other, into a trained model. Alternatively, the processing circuitry 11 may generate a plurality of ACT coefficient datasets by performing orthogonal transform on a plurality of medical raw datasets respectively corresponding to a plurality of components, input a residual error between the plurality of ACT coefficient datasets, and output a blend dataset. By inputting of a residual error into a trained model in this manner, the number of layers for the trained model can be decreased.

(Fifth Modification)

The above embodiment was described based on the premise that a plurality of medical raw datasets respectively corresponding to a plurality of components are compressed. However, the present embodiment is not limited to this. Data to be compressed may be any data including datasets respectively corresponding to components. For example, medical image datasets respectively corresponding to components may be compressed. For example, data to be compressed may be a plurality of CT image datasets respectively corresponding to a plurality of tube voltages, a plurality of CT image datasets respectively corresponding to a plurality of energy bins, or a plurality of MR image datasets respectively corresponding to a plurality of receiver channels. Similarly, a compressed dataset obtained by compressing a plurality of medical image datasets respectively corresponding to a plurality of components may be decoded. In this manner, data is decoded from a compressed dataset. Examples of compressed data include a plurality of CT image datasets respectively corresponding to a plurality of tube voltages, a plurality of CT image datasets respectively corresponding to a plurality of energy bins, and a plurality of MR image datasets respectively corresponding to a plurality of receiver channels.

According to at least one of the embodiments described above, the efficiency of compression and/or decoding with respect to multicomponent medical data can be improved.

The term "processor" used in the above explanation indicates, for example, a circuit, such as a CPU, a GPU, or an Application Specific Integrated Circuit (ASIC), and a programmable logic device (for example, a Simple Programmable Logic Device (SPLD), a Complex Programmable Logic Device (CPLD), and a Field Programmable Gate Array (FPGA)). A processor realizes its functions by reading and executing a program stored in memory circuitry. Instead of storing a program on memory circuitry, a program may be directly integrated into circuitry of a processor. In this case, a processor reads and executes a program integrated into circuitry, thereby realizing its functions. The function corresponding to the program may be realized by a combination of logic circuits, not by executing the program. Each processor of the present embodiment is not limited to a configuration as a single circuit; a plurality of independent circuits may be combined into one processor to realize the function of the processor. Furthermore, a plurality of constituent elements shown in FIGS. 1, 14, and 15 may be integrated into one processor to realize their functions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical data processing apparatus, comprising:
processing circuitry configured to
obtain a compressed channel of data generated by compressing a plurality of first medical channels of data defined by a first domain representation, and respectively corresponding to a plurality of components, via an intermediate channel of data defined by a second domain representation; and
decode the compressed channel of data to a second medical channel of data defined by the first domain representation based on a conversion process from the plurality of first medical channels of data to the compressed channel of data,
wherein the processing circuitry is further configured to generate a decoded intermediate channel of data defined by the second domain representation by performing entropy decoding and inverse quantization on the compressed channel of data, and generate the second medical channel of data by performing inverse base conversion on the decoded intermediate channel of data.

2. The medical data processing apparatus according to claim 1 wherein:
the first domain representation includes a dimension of a spatial domain and a dimension of a component domain; and
the second domain representation includes a dimension of a spatial frequency domain.

3. The medical data processing apparatus according to claim 1, wherein the processing circuitry is further configured to decode the compressed channel of data to the second medical channel of data with respect to all of the components or a selected component of the components.

4. The medical data processing apparatus according to claim 1, wherein the processing circuitry is further configured to execute inverse orthogonal conversion as the inverse base conversion.

5. The medical data processing apparatus according to claim 1, wherein the processing circuitry is further configured to use, as the inverse base conversion, a trained model trained in such a manner that the intermediate channel of data is input and the second medical channel of data is output.

6. The medical data processing apparatus according to claim 5, further comprising:
a memory configured to store a plurality of trained models in such a manner that the trained models are correlated with a plurality of imaging body parts, wherein the processing circuitry is further configured to select, from the plurality of trained models, a trained model correlated with an imaging body part relating to the compressed channel of data.

7. The medical data processing apparatus according to claim 5, wherein the processing circuitry is further configured to perform prediction in units of a number of rows in an X-ray detector or in units of blocks equal to an integral multiple of a number of echo trains.

8. The medical data processing apparatus according to claim 1, wherein the plurality of first medical channels of data are generated in units of a number of rows in an X-ray detector or in units of blocks equal to an integral multiple of a number of echo trains.

9. The medical data processing apparatus according to claim 1, wherein the plurality of components correspond to a plurality of tube voltages in a dual energy scan, a plurality of energy bins in photon counting CT, and a plurality of receiver channels in magnetic resonance imaging.

10. The medical data processing apparatus according to claim 1, wherein the compressed channel of data contains information on all or part of the plurality of components.

11. The medical data processing apparatus according to claim 1, wherein the processing circuitry is further configured to generate the compressed channel of data from the plurality of first medical channels of data.

12. A medical data processing method, comprising:
obtaining compressed data acquired by compressing a plurality of first medical channels of data defined by a first domain representation, and respectively corresponding to a plurality of components, via an intermediate channel of data defined by a second domain representation; and
decoding the compressed channel of data to the second medical channel of data defined by the first domain representation based on a conversion process from the plurality of first medical channels of data to the compressed channel of data,
wherein the method further comprises generating a decoded intermediate channel of data defined by the second domain representation by performing entropy decoding and inverse quantization on the compressed channel of data, and generating the second medical channel of data by performing inverse base conversion on the decoded intermediate channel of data.

13. A medical image diagnostic apparatus, comprising:
a gantry configured to acquire a plurality of first medical channels of data defined by a first domain representation, and respectively corresponding to a plurality of components; and
processing circuitry configured to generate compressed data by compressing the plurality of first medical channels of data via an intermediate channel of data defined by a second domain representation,
wherein the processing circuitry is further configured to generate the intermediate channel of data defined by the second domain representation by performing base conversion on the plurality of first medical channels of data to generate the compressed data by performing quantization and entropy coding on the intermediate channel of data.

14. The medical image diagnostic apparatus according to claim 13, further comprising a display, wherein:
the processing circuitry is further configured to decode the compressed data to a second medical dataset defined by the first domain representation based on a conversion process from the plurality of first medical channels of data to the compressed data, and reconstruct a medical image based on the second medical channel of data; and
the display displays the medical image.

* * * * *